(12) United States Patent
Mackool et al.

(10) Patent No.: US 10,561,313 B2
(45) Date of Patent: Feb. 18, 2020

(54) REFRACTION DEVICES

(71) Applicant: Accuvisiondesigns LLC, Farmingdale, NY (US)

(72) Inventors: Richard James Mackool, Sarasota, FL (US); Richard Jonathan Mackool, Pelham, NY (US); Brice Kaleski, Simi Valley, CA (US); Robert R. Towle, Wantagh, NY (US); Evan Rittenhouse Jones, Levittown, NY (US); Christopher Dean Smith, Shirley, NY (US)

(73) Assignee: ACCUVISIONDESIGNS LLC, Farmingdale, NY (US)

( * ) Notice: Subject to any disclaimer, the term of this patent is extended or adjusted under 35 U.S.C. 154(b) by 102 days.

(21) Appl. No.: 15/785,984

(22) Filed: Oct. 17, 2017

(65) Prior Publication Data

US 2019/0110679 A1    Apr. 18, 2019

(51) Int. Cl.

| *A61B 3/02* | (2006.01) |
|---|---|
| *A61B 3/103* | (2006.01) |
| *A61B 3/00* | (2006.01) |
| *G02C 7/02* | (2006.01) |
| *A61B 3/06* | (2006.01) |
| *A61B 3/11* | (2006.01) |
| *A61B 3/113* | (2006.01) |
| *A61B 3/032* | (2006.01) |
| *A61B 3/036* | (2006.01) |

(52) U.S. Cl.
CPC ............. *A61B 3/103* (2013.01); *A61B 3/005* (2013.01); *A61B 3/0008* (2013.01); *A61B 3/0025* (2013.01); *A61B 3/032* (2013.01); *A61B 3/063* (2013.01); *A61B 3/112* (2013.01); *A61B 3/113* (2013.01); *G02C 7/024* (2013.01); *A61B 3/0083* (2013.01); *A61B 3/036* (2013.01); *A61B 3/111* (2013.01)

(58) Field of Classification Search
CPC ....... A61B 3/0025; A61B 3/036; A61B 3/028; A61B 3/103; A61B 5/117; A61F 2002/1699; A61F 2/1645; A61F 2/1654; A61F 9/013; A61F 2009/00846; A61F 2009/00848; A61F 2009/00872; A61F 9/00806
USPC ........ 351/200, 205–206, 209–211, 221, 222, 351/235
See application file for complete search history.

(56) References Cited

U.S. PATENT DOCUMENTS

| 7,156,517 B2 | 1/2007 | Hosoi |
|---|---|---|
| 7,289,254 B2 | 10/2007 | Avudainayagam et al. |

(Continued)

OTHER PUBLICATIONS

International Search Report and Written Opinion of the International Searching Authority, dated Dec. 26, 2018, corresponding to counterpart International Application No. PCT/US2018/056034; 9 total pages.

*Primary Examiner* — Brandi N Thomas
(74) *Attorney, Agent, or Firm* — Carter, DeLuca & Farrell, LLP

(57) ABSTRACT

A refraction device includes a main body, a spherical power lens coupled to the main body, an astigmatic power lens movably coupled to the main body, and a visual display coupled to the main body and oriented toward an optical pathway extending through the spherical power lens and the astigmatic power lens. The visual display is configured to display an image for testing visual acuity.

20 Claims, 16 Drawing Sheets

(56) References Cited

U.S. PATENT DOCUMENTS

| | | | |
|---|---|---|---|
| 8,182,091 B2 | 5/2012 | Foster | |
| 2003/0090630 A1* | 5/2003 | Biggins | A61B 3/0285 351/233 |
| 2006/0050238 A1* | 3/2006 | Nakamura | A61B 3/0041 351/205 |
| 2014/0266986 A1* | 9/2014 | Magyari | G02B 27/0172 345/8 |
| 2016/0310000 A1* | 10/2016 | Meneghini | A61B 3/0075 |

* cited by examiner

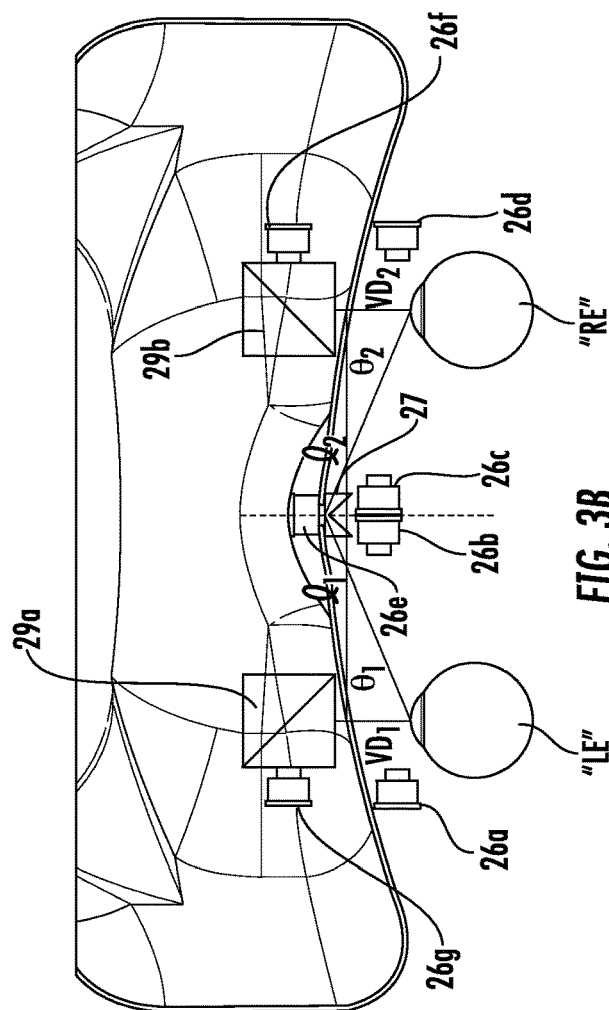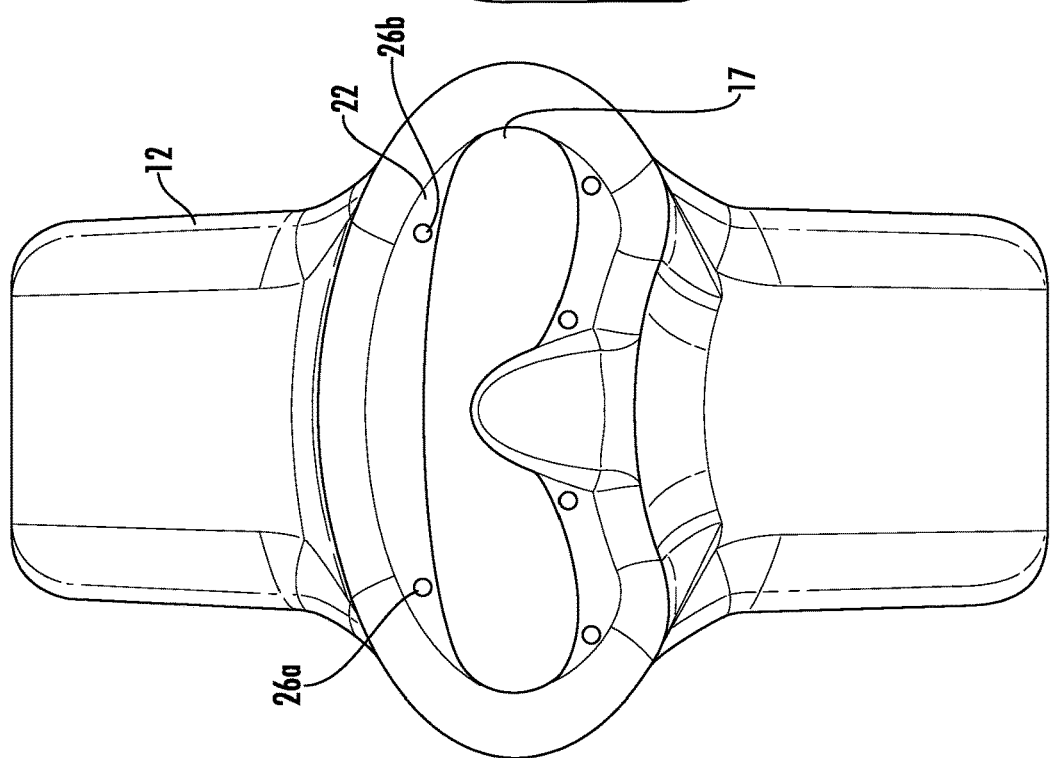
FIG. 3B
FIG. 3A

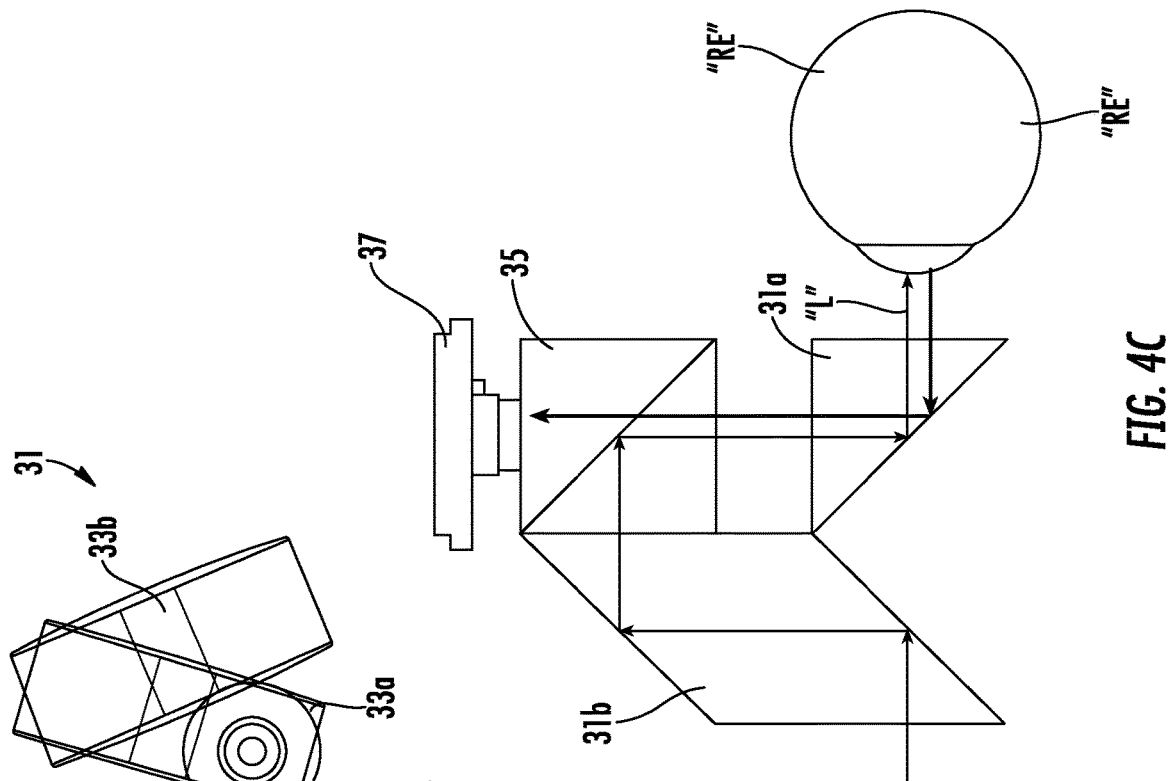
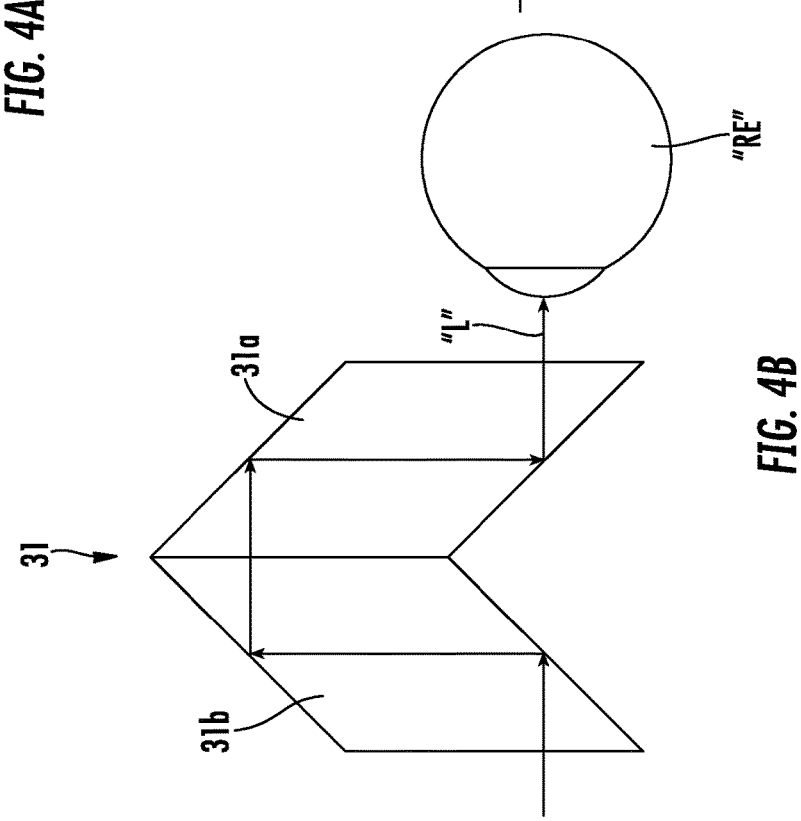
FIG. 4A
FIG. 4B
FIG. 4C

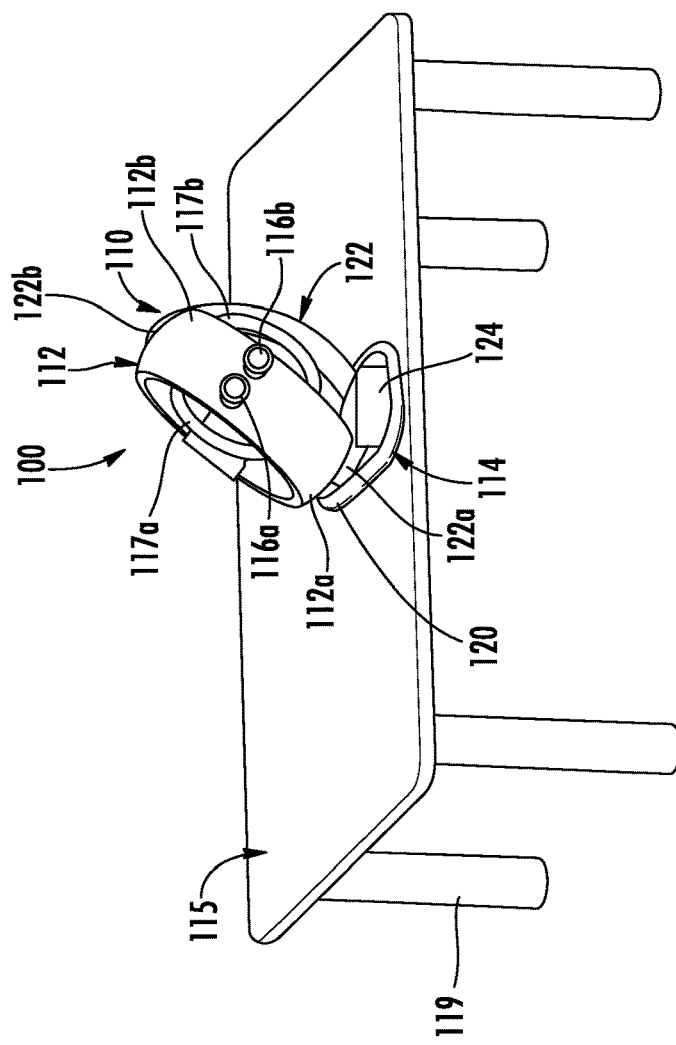
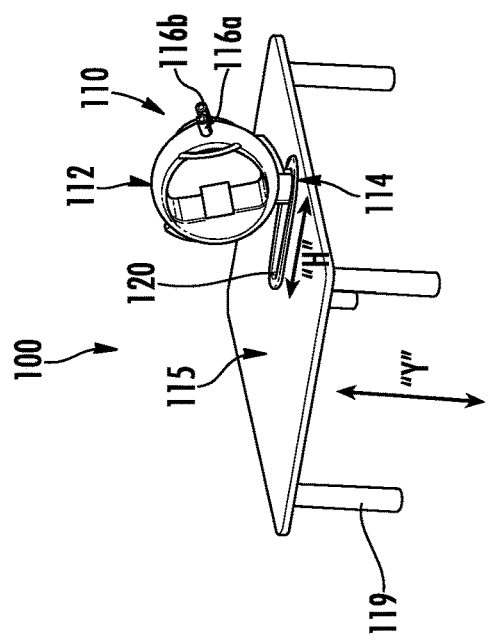
FIG. 15B
FIG. 15A

REFRACTION DEVICES

BACKGROUND

Refraction devices are ophthalmic diagnostic instruments that measure a variety of refractive errors of a patient's eye. An eye care professional may utilize the measurements taken by a refraction device to determine, inter alia, a patient's corrective lens prescription. During use of a refraction device, a patient looks into an adjustable eyepiece of the refraction device to view an eye chart positioned a selected distance away. As the patient is viewing the eye chart, the eye care professional adjusts various optical lens elements of the refraction device based on subjective feedback provided by the patient on whether an adjusted optical element improves or degrades visual acuity.

Typically, the patient's participation in an eye examination generally does not extend beyond providing responses to cues from the eye care professional. Thus, while the patient does have some input during the refraction process, control over the adjustments to the optical elements of the refraction device is solely in the hands of the eye care professional. In this way, the degree of accuracy of the measurements is vulnerable to any faulty communication between patient and professional. Further, since the patient is only partially responsible for the outcome of the eye examination, if the patient is displeased with the prescription of the resulting eyewear, the patient may be inclined to place the sole blame on the eye care professional rather him or herself. As such, eye care professionals and patients alike may benefit from increasing patient involvement in the refraction process. This can result in an increase in the accuracy of the measurements and an improvement in the confidence of the patient in the final determined prescription.

Accordingly, there is a need for refraction devices that provide patients with more control over the eye examination process. In addition, it would be desirable to provide a refraction device that creates a more intuitive experience for the patient, has improved accuracy in taking refractive error measurements, and is more handicap-accessible.

SUMMARY

In accordance with an aspect of the present disclosure, a patient-operable refraction device is provided. The refraction device includes a main body, a spherical power lens coupled to the main body, an astigmatic power lens movably coupled to the main body, and a visual display coupled to the main body and oriented toward an optical pathway extending through the spherical power lens and the astigmatic power lens. The visual display is configured to display an image for testing visual acuity.

In embodiments, the refraction device may include a plurality of astigmatic power lenses. Each of the astigmatic power lenses may be configured to be selectively moved between a position in line with the spherical power lens, and a position out of line with the spherical power lens.

In embodiments, the refraction device may include a belt disposed within the main body and having the astigmatic power lenses associated therewith. One or more of the astigmatic power lenses may be rotatable relative to the belt.

In embodiments, the belt may be movable relative to the main body to position a selected astigmatic power lens in line with the spherical power lens.

In embodiments, the belt may have an arcuate configuration such that the belt is movable relative to the main body along a circular pathway.

In embodiments, the belt may have a plurality of brackets coupled to one another. Each astigmatic power lens may be coupled to a respective bracket of the plurality of brackets.

In embodiments, an astigmatic power lens may be rotatable relative to a respective bracket to adjust an axis of the astigmatic power lens.

In embodiments, the refraction device may include a plurality of brackets disposed within the main body. Each astigmatic power lens may be coupled to a respective bracket. The plurality of brackets may be coupled to one another and disposed in an annular array.

In embodiments, the refraction device may include a wheel rotatably supported in the main body. The brackets may be circumferentially disposed on the wheel. The rotatable wheel may include a plurality of circumferentially-disposed rails extending laterally therefrom. The brackets may be slidably supported on the rails such that a horizontal position of the brackets relative to the wheel is adjustable to align a selected one of the astigmatic power lenses with a patient's pupil.

In embodiments, the refraction device may include a tunable prism disposed in line with the spherical power lens and the astigmatic power lens. The tunable prism may be configured to redirect light passing from the visual display to a patient's eye In embodiments, the refraction device may include a prism lens assembly disposed in line with the spherical power lens and the astigmatic power lens. The prism lens assembly may be movable between a linear configuration, in which light passes linearly therethrough, and at least one non-linear configuration, in which the prism lens assembly redirects light passing therethrough. The prism lens assembly may include a pair of outer plates and an inner optical element disposed between the outer plates. One or more of the plates may be movable to adjust the inner optical element between the linear and at least one non-linear configurations.

In embodiments, the visual display may be a heads-up display disposed on a distal side of the main body. The heads-up display may be configured to display an eye chart.

In embodiments, the visual display may be configured to project a hologram of an eye chart in a format that is equivalent to reading the eye chart at a distance of approximately 20 feet.

In embodiments, the main body may define a cavity therein, and the visual display may be spaced across the cavity from each of the first eyepiece, the spherical power lens, and the astigmatic power lens.

In another aspect of the present disclosure, a patient-operable refraction device is provided and includes a main body, a spherical power lens coupled to the main body, a plurality of astigmatic power lenses, a plurality of brackets disposed within the main body, and a visual display coupled to the main body. The brackets have the astigmatic power lenses associated therewith, and the brackets are movable relative to the main body to position a selected astigmatic power lens in line with the spherical power lens. The visual display is oriented toward an optical pathway extending through the spherical power lens and the selected astigmatic power lens. The visual display is configured to display an image for testing visual acuity.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIG. 3A is a front view of the refraction device shown in FIG. 2B illustrating a plurality of sensors coupled to a main body of the refraction device;

FIG. 3B is a top view of the refraction device of FIG. 3A illustrating the plurality of sensors;

FIG. 4A is a rear view of a prism assembly for use in the refraction device of FIG. 1;

FIG. 4B is a side view of the prism assembly of FIG. 4A;

FIG. 4C is a side view of another embodiment of a prism assembly for use in the refraction device of FIG. 1;

FIG. 13B is a front view of the refraction device of FIG. 13A illustrating a pair of lens units in an adjusted position to account for a patient's pupillary distance;

FIG. 15A is perspective view of an eye examination system including a table and a refraction device supported on the table illustrating a main body of the refraction device coupled to a base;

FIG. 15B is another perspective view of the refraction device of FIG. 15A illustrating the main body of the refraction device in a tilted orientation relative to the base;

DETAILED DESCRIPTION

Figure 1:
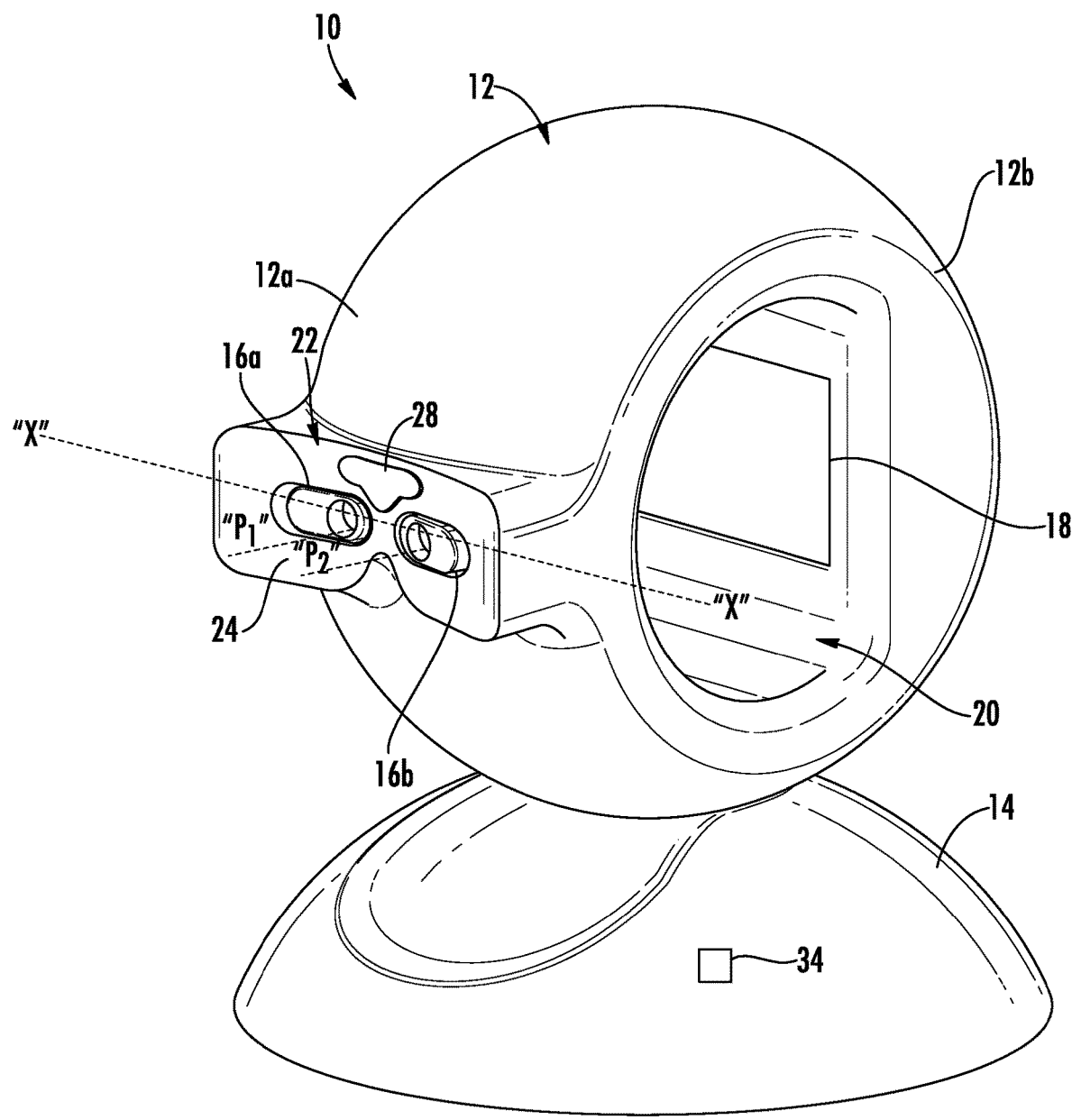
FIG. 1 is a perspective view of a refraction device for determining refractive errors of a patient's eye(s) in accordance with an embodiment of the present disclosure.

Embodiments of the presently disclosed refraction devices and eye examination systems are described in detail with reference to the drawings, in which like reference numerals designate identical or corresponding elements in each of the several views. As used herein and as is traditional, the term "distal" will refer to that portion of the refraction device which is further from the user while the term "proximal" will refer to that portion of the refraction device which is closer to the user.

The present disclosure provides a patient-operable refraction device that gives a patient control over administering an eye examination (e.g., a visual acuity test). The refraction device includes a main body or housing, a pair of eyepieces extending from the main body, and a lens assembly disposed within the main body. The lens assembly includes an adjustable spherical power lens and a plurality of astigmatic power lenses coupled to a belt that moves through the main body of the refraction device to selectively position one of the astigmatic power lenses into an optical pathway of one of the eyepieces. The refraction device may also include a visual display for displaying an image (e.g., an eye chart) used for testing visual acuity. The visual display may be formed with the main body such that the lens assembly, the main body, and the visual display are one integral unit. In some embodiments, the refraction device may also include an adjustable prism power lens for determining eye alignment issues. As such, the refraction device may provide testing of fine vision correction (e.g., spherical power and/or astigmatic power correction) and measurement and correction of ocular misalignment, e.g., phoria or tropia.

Referring to FIG. 1, illustrated is a patient-operable refraction device 10 for determining refractive errors of a patient's eyes. The refraction device 10 generally includes a main body or housing 12 coupled to a base 14, a pair of elongated eyepieces 16a, 16b, diagnostic lenses (e.g., a pair of spherical power lens assemblies 30a, 30b and a pair of astigmatic power belts 50a, 50b), and a visual display 18 formed with the main body 12.

The main body 12 has a generally spherical shape and defines a centrally-located cavity 20 extending transversely therethrough. In some embodiments, the main body 12 may assume a variety of shapes, such as, for example, a square, a dome, an ellipse, or the like. The main body 12 includes a proximal side 12a having the spherical power lens assemblies 30a, 30b disposed therein, and a distal side 12b having the visual display 18 disposed therein.

Figure 2C:
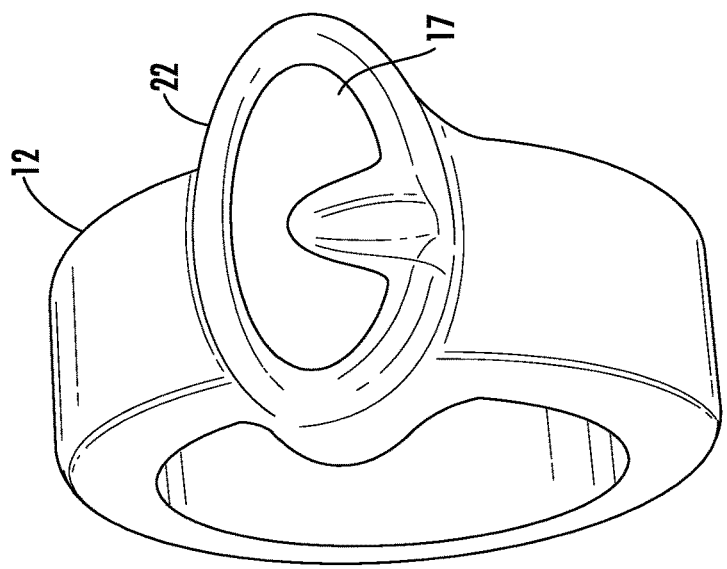
FIGS. 2A-2C are perspective views of alternative embodiments of eyepieces used in the refraction device of FIG. 1.
Figure 2B:
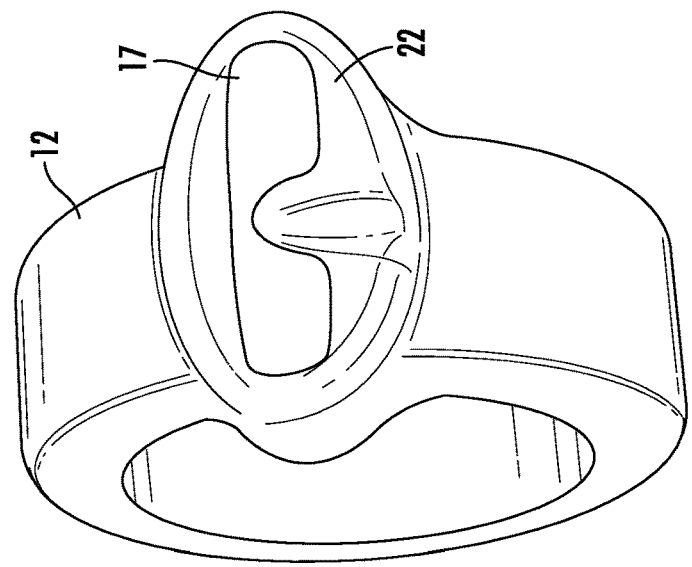
Figure 2A:
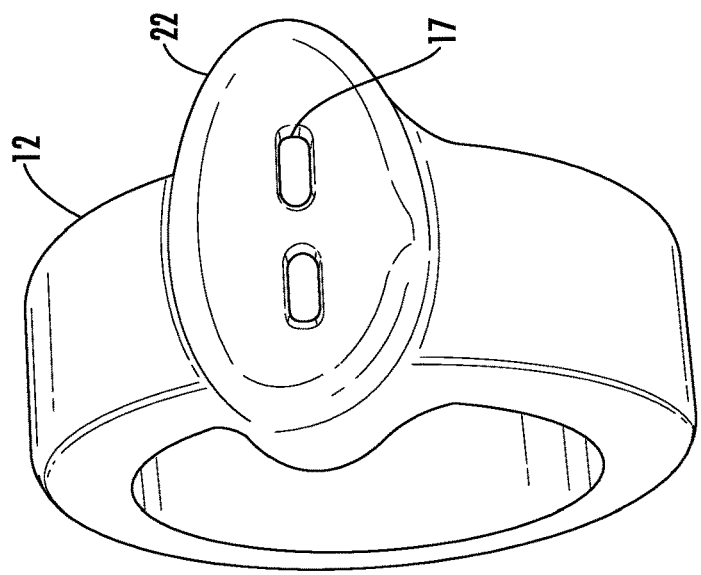

The first and second eyepieces 16, 16b are horizontally-spaced from one another and extend through a face mount 22 formed with the proximal side 12a of the main body 12. The eyepieces 16a, 16b allow light to pass therethrough and into the cavity 20 of the main body 12. The eyepieces 16a, 16b may be movable or slidable along a horizontal axis "X" relative to one another to adjust the horizontal distance between the eyepieces 16a, 16b to match the pupillary distance ("PD") of a patient's eyes. With brief reference to FIGS. 2A, 2B, and 2C, in other embodiments, rather than having elongated eyepieces 16a, 16b, the refraction device 10 may have one or two eyepieces 17 configured as a transparent sheet or plate of material (e.g., plastic) that is disposed in front of the diagnostic lenses.

With continued reference to FIG. 1, the main body 12 includes a face mount 22 extending proximally from the proximal side 12a of the main body 12. In some embodiments, the face mount 22 may be integrally connected to or monolithically formed with the main body 12. The face mount 22 defines a concave outer surface 24 dimensioned for supporting a forehead of a patient. The main body 12 may include a support member 28 attached to the face mount 22 for supporting a forehead of a patient. The support member 28 projects proximally from the outer surface 24 of the face mount 22 to maintain a forehead of a patient at a selected distance from the outer surface 24 of the face mount 22. The support member 28 is configured to move relative to and within the face mount 22 to adjust the distance the support member 28 projects from the outer surface 24 of the face mount 22.

With reference to FIGS. 3A and 3B, the main body 12 includes a plurality of sensors 26a-g disposed adjacent the eyepiece 17. The sensors 26a-g may be camera sensors or configured to measure a position of an object (e.g., an eye pupil). It is contemplated that the sensors 26a-g may be any suitable sensor for measuring a position of an object, including, but not limited to, proximity sensors, image sensors, infrared sensors, ultrasonic sensors, or the like. The sensors 26a-g are configured to measure a vertex distance of a patient wearing corrective lenses (i.e., the distance between the outer surface of a patient's eye and the back of an ophthalmic lens worn by the patient), and a pupillary distance of a patient's eyes when a patient is looking through the eyepiece 17. The refraction device 10 may include a processor (not shown) and a motor (not shown) in communication with the sensors 26a-26g.

First and second sensors 26a, 26b may project from the face mount 22 and be oriented horizontally, such that the first and second sensors 26a, 26b track opposite sides of a left eye of a patient. Third and fourth sensors 26c, 26d may project from the face mount 22 and be oriented horizontally, such that the third and fourth sensors 26c, 26d track opposite sides of a right eye of a patient. A double prism 27 may be positioned at a central location of the face mount 22 along with a sixth camera 26e. Two additional cameras 26f, 26g may be disposed within the main body 12 behind the respective lens assemblies 30a, 30b along with associated beam splitters 29a, 29b.

To determine the vertex distance of a patient, a patient places their eyes "LE," "RE" into the eyepiece 17 while wearing their eyewear. The sensors 26a-g determine the distance between the outer surface of the patient's eyes and the back of their ophthalmic lens (i.e., the vertex distance). The data from the sensors 26a-g is correlated to triangulate the position of the patient's pupils. An example configuration would be to have two cameras 29a, 29b with beam splitters with a view optically coaxial to the patient's eyes in conjunction with one centrally positioned camera 26e optically coupled with a double prism to view both of the patient's pupils from the side. Once the optically coaxial cameras 29a, 29b are aligned with the patient's pupils, using any of the mechanisms described below, the distance l1 and l2 is known. By combining the distances l1 and l2 with angles θ1 and θ2 measured by the centrally mounted camera 26e, the vertex distances VD1 and VD2 can be determined as follows:

$$VDn = ln \tan(\theta n)$$

The measured vertex distance may be stored in a memory of the refraction device 10 and/or sent to a patient record system to be accessed at a subsequent eye examination. After the vertex distance is determined, the patient removes the eyewear and places their forehead against the outer surface 24 of the face mount 22 to align their eyes with optical pathways "P1," "P2" (FIG. 1) defined through the respective first and second eyepieces 16a, 16b and respective left and right side diagnostic lenses. With the patient's forehead resting on the face mount 22, the processor communicates to a motor (not shown) to move the support member 28 in a proximal direction relative to the outer surface 24 of the face mount 22.

While the support member 28 is being moved, the sensors 26a-g are configured to continuously measure the distance between the outer surface of the patient's eye and a spherical power lens 32 (FIG. 7) of the refraction device 10. The processor ceases adjusting the support member 28 upon the sensors 26a-g determining that the distance between the outer surface of the patient's eyes and a spherical power lens 32 of the refraction device 10 matches the prior-measured vertex distance. With the support member 28 set in this position, the patient's eyes will be spaced from the spherical power lens 32 at approximately or exactly the measured vertex distance. As such, a visual acuity test will be conducted with the patient's eyes at the particular vertex distance the patient usually wears their eyewear.

The sensors or camera 26a-g may also determine the patient's pupillary distance and communicate the determined pupillary distance to the processor. In response, the processor may automatically activate the motor to move the eyepieces 16a, 16b along the horizontal axis "X" to match the horizontal distance the eyepieces 16a, 16b are spaced from one another with the determined pupillary distance. Alternatively or additionally, the processor may automatically activate the motor to move the diagnostic lenses along the horizontal axis "X" to match the horizontal distance the left and right side diagnostic lenses are spaced from one another with the determined pupillary distance. In some embodiments, instead of translating the eyepieces 16a, 16b along the horizontal axis "X," the eyepieces 16a, 16b may be pivoted to move proximal ends thereof either toward one another or away from one another to adjust the pupillary distance.

As can be appreciated, the eyepieces 16a, 16b are adjusted to match the PD of the patient, the eyepieces 16a, 16b may become misaligned with the diagnostic lenses of the refraction device 10 (e.g., the spherical power lens assemblies 30a, 30b and the astigmatic power lenses 54, which will be described in detail below). To realign the optical pathway to be between the diagnostic lenses and the patient's eyes, the refraction device 10 may include a prism assembly 31, as shown in FIGS. 4A-4D.

Figure 6:
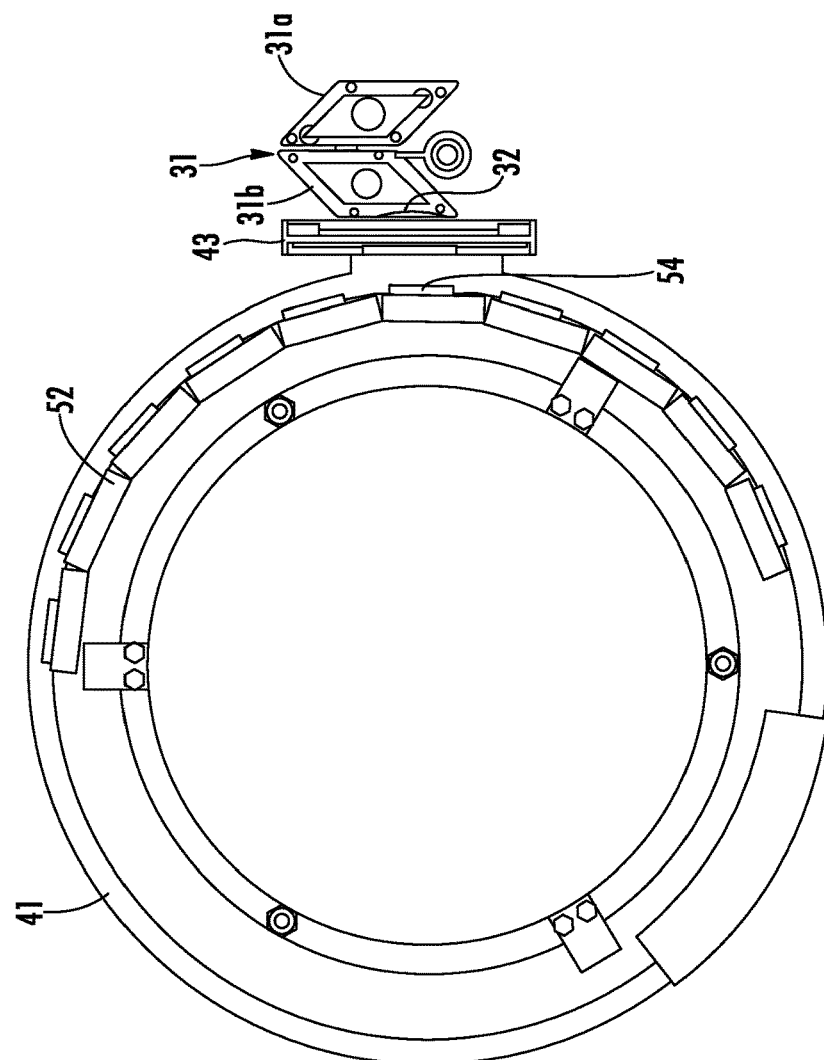
FIG. 6 is a cross-sectional view, taken alone line 6 of FIG. 5, of the internal components of the refraction device.

With reference to FIGS. 4A, 4B, and 6, the prism assembly 31 includes a first pair of prisms 31a, 31b located behind or distal the first eyepiece 16a, and a second pair of prisms 33a, 33b located behind or distal the second eyepiece 16b. Each of the first and second pair of prisms 31a, 31b, 33a, 33b includes a proximal prism 31a, 33a and a distal prism 31b, 33b. The proximal prism 31a, 33a has a proximal end aligned with and rotatably coupled to the respective eyepieces 16a, 16b, and a distal end rotatably coupled to a proximal end of the distal prism 31b, 33b. The distal prism 31b, 33b has a distal end aligned with the diagnostic lenses. It is contemplated that each of the pairs of prisms 31a, 31b and 33a, 33b may be coupled to one another via any suitable fastening engagement, including fasteners, bearings, hinges, or the like. The prism assembly 31 is configured to receive light "L" entering in a first direction, and redirecting or shifting the light in a horizontal direction to ensure the patient's eyes receive the light regardless of the horizontal position of the patient's eyes relative to the diagnostic lenses.

The prisms 31a, 31b, 33a, 33b may be any suitable prism such as rhomboid prisms, right angle prisms, or any combination thereof. For example, as shown in FIGS. 4A and 4B, the proximal and distal prisms 31a, 31b may each be a rhomboid prism, or as shown in FIG. 4C, the proximal and distal prisms 31a, 31b may be a rhomboid prism and a right angle prism, respectively. In the embodiment illustrated in FIG. 4C, the prism assembly 31 further includes a beam splitter 35 and an eye-tracking camera or sensor 37 for measuring the PD of a patient's eyes by determining the position of the patient's pupils.

In use, as the eyepieces 16a, 16b are moved to match the PD of a patient's eyes, or in any instance where the diagnostic lenses are out of alignment with the patient's pupils, the front or proximal prism 31a and 33a of each of the two pairs of prisms moves with the eyepieces 16a, 16b. While this movement of the eyepieces 16a, 16b may cause the eyepieces 16a, 16b, and in turn the patient's pupils, to become misaligned with the diagnostic lenses (e.g., the spherical power lenses 30a, 30b), the optical pathway extending between the diagnostic lenses and the patient's eyes is maintained by the prism assembly 31. One benefit of the prism assembly 31 is that it allows for adjusting the optical pathway to match the patient's PD without having to move any of the diagnostic lenses, and in some embodiments, the eyepieces 16a, 16b.

In embodiments, rather than having a patient or technician manually adjust the eyepieces 16a, 16b, the eye tracking camera 37 of the prism assembly 31 may determine the patient's PD, and communicate with the processor to automatically adjust the eyepieces 16a, 16b to match the patient's determined PD. In other embodiments, as mentioned above, the refraction device 10 may have an eyepiece 17 (FIGS. 2A-2C) that includes a fixed transparent plate that is disposed in front of the prism assembly 31 and the diagnostic lenses. In this embodiment, the processor may be configured to automatically adjust the prism assembly 31, based on the patient's determined PD, to ensure the optical pathway passes through the diagnostic lenses and into the patient's pupils.

Figure 4D:
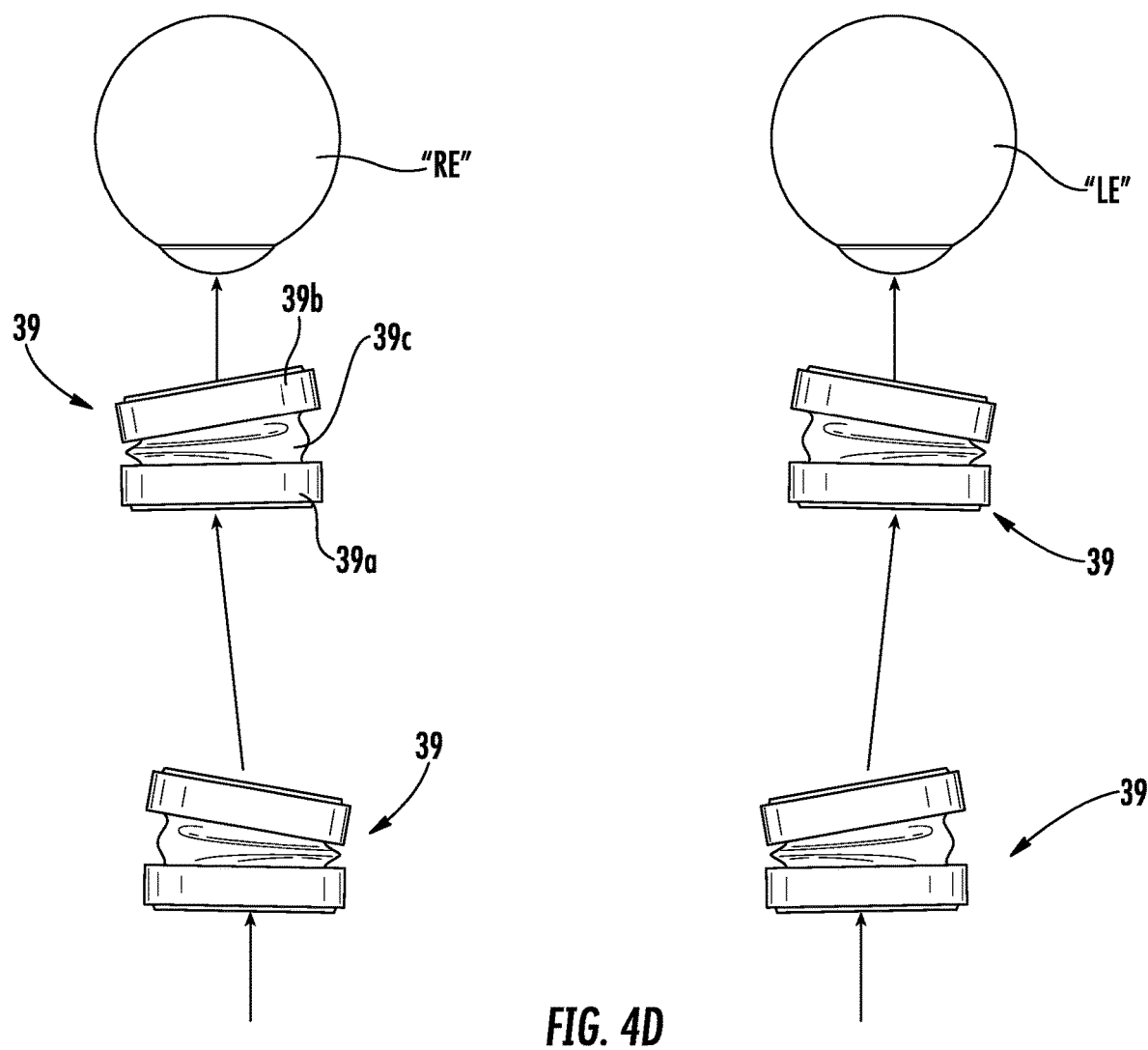
FIG. 4D is a top view of yet another embodiment of a prism assembly for use in the refraction device of FIG. 1.

With reference to FIG. 4D, an alternative embodiment of a prism assembly is illustrated and includes a pair of optical elements 39 (e.g., a tunable prism) aligned with one another and the diagnostic lenses. Each of the optical elements 39 includes two outer lenses 39a, 39b and an inner membrane or diaphragm 39c pivotably coupling the outer lenses 39a, 39b to one another. Upon pivoting the outer lenses 39a, 39b relative to one another about the inner diaphragm 39c, the optical element 39 is transitioned from a linear configuration to a non-linear configuration. In the linear configuration, light passes linearly through the optical element 39. In the non-linear configuration, light passes from the first outer lens 39a of the optical element 39 in a first direction, and is then shifted as it passes through the diaphragm 39c and the second outer lens 39b. In this way, manipulation of the optical elements 39 provides control over the direction light that passes through it. In embodiments, the prism assembly 31 may only include one optical element 39 rather than a pair of optical elements 39.

With reference to FIGS. 1 and 5-7, the refraction device 10 includes an annular frame 41 disposed within the main body 12, and a pair of lens assemblies 30a, 30b coupled to the frame 41 via a bracket 43. The pair of lens assemblies 30a, 30b are each disposed behind (i.e., distally of) the respective eyepieces 16a, 16b and in line with the optical pathways "P1," "P2" defined by each of the eyepieces 16a, 16b. Since each of the lens assemblies 30a, 30b are substantially similar, only a first lens assembly 30a of the pair of lens assemblies 30a, 30b will be described in detail herein.

The lens assembly 30a includes an adjustable spherical power lens 32, a power wheel 36 disposed behind the spherical power lens 32, and a cylindrical fine adjustment wheel 45 (not shown in FIG. 7) disposed behind the power wheel 36. The spherical power lens 32 is an adjustable focus lens for correcting a spherical power of an eye in about 0.25 diopter steps or increments. In some embodiments, the spherical power lens 32 may be an electrically tunable lens, a lower-power liquid lens, or any other suitable spherical power lens capable of adjusting its power in response to an application of electrical or mechanical energy.

The lens assembly 30a may include a power supply (not shown), a discreet controller, and/or other electronics such as a wireless transmitter and/or a receiver in communication with the spherical power lens 32 for selectively adjusting the power thereof. The power of the spherical power lens 32 may be adjusted by rotating the eyepiece 16a. In other embodiments, the refraction device 10 may include a control 34 (e.g., a dial, button, touch pad, etc.) coupled to the main body 12 or the base 14 and which may be manually adjusted by the patient or a technician to adjust the power of the spherical power lens 32 in increments of 0.25D, 0.5D, 0.75D, 1.0D, or any suitable step of diopters. In embodiments, the control 34 may be remote from the refraction device 10.

The power wheel 36 of the lens assembly 30a is disc-shaped and has a plurality of openings 38a, 38b, 38c, 38d disposed in an annular array about a center point of the power wheel 36. The power wheel 36 is rotatably supported in the proximal side 12a of the main body 12 between the adjustable spherical power lens 32 and a cylindrical power lens 54. In some embodiments, the power wheel 36 may be located proximally of the adjustable spherical power lens 32 rather than distally. One opening 38a in the power wheel 36 may be devoid of a power lens, and another opening 38b in the power wheel 36 may include blackout lens 40 that prevents the passage of light therethrough.

The power wheel 36 is configured to adjust the spherical power in larger diopter increments than the adjustable spherical power lens 32. For example, the power wheel 36 may include two spherical power lenses 42, 44 disposed in respective openings 38c, 38d and having a power of +10.00D and −10.00D, respectively. In some embodiments, the power lenses 42, 44 of the power wheel 36 may have more or less power than + or −10.00D. It is contemplated that the power wheel 36 may have more than two spherical power lenses such that the power wheel 36 can adjust the power in more steps than + or −10.00D (e.g., + or −5.00D, + or −2.50D, or + or −1.25D).

With continued reference to FIGS. 1 and 5-7, the frame 41 is rotatably fixed within the main body 12 and supports first and second wheels 47a, 47b on opposite sides of the frame 41. The frame 41 defines annular tracks in opposite sides thereof having the respective first and second wheels 47a, 47b movably disposed therein. As such, the wheels 47a, 47b are each independently movable along the circumference of the frame 41. Each of the wheels 47a, 47b may have a toothed, flexible band (not explicitly shown) fixed to an outer or inner periphery thereof and in communication with a motorized gear for transferring rotational motion to the wheels 47a, 47b.

The refraction device 10 further includes first and second belts, tracks, or chains 50a, 50b fixed to respective first and second wheels 47a, 47b. In embodiments, the belts 50a, 50b may be monolithically formed with the wheels 47a, 47b. The belts 50a, 50b are disposed in side-by-side relation to one another, wherein the first belt 50a is coplanar with the left spherical power lens 32 and the first eyepiece 16a and the second belt 50b is coplanar with the right spherical power lens 32 and the second eyepiece 16b. Since the first and second belts 50a, 50b and their components are substantially similar to one another, only the first belt 50a and its components will be described in detail herein.

The belt 50a extends through a circular channel (not explicitly shown) defined through the main body 12 giving belt 50a an arcuate configuration. The belt 50a may be one continuous loop that extends around an entire circumference of the main body 12 or, in some embodiments, the belt 50a may only extend partially around the circumference of the main body 12. As briefly mentioned above, the main body 12 may include a pair of flexible bands fixed to an inner periphery of the first and second wheels 47a, 47b. The flexible bands may be operably coupled to two discreet motors for rotating the belts, and in turn the wheels 47a, 47b and the belts 50a, 50b. The motors may have gears (e.g., a pinion gear) coupled to gear teeth on an inner periphery of the flexible bands to operably couple the motor and the flexible band. As will be described in detail below, the belt 50a is movable (e.g., rotatable) through the circular channel of the main body 12 to selectively adjust a cylindrical power of the refraction device 10 by positioning a selected bracket 52 of the belt 50a and, in turn, an associated astigmatic power lens 54, in line with the optical pathway "P1" of the first eyepiece 16a and the left pupil of a patient.

Figure 5:
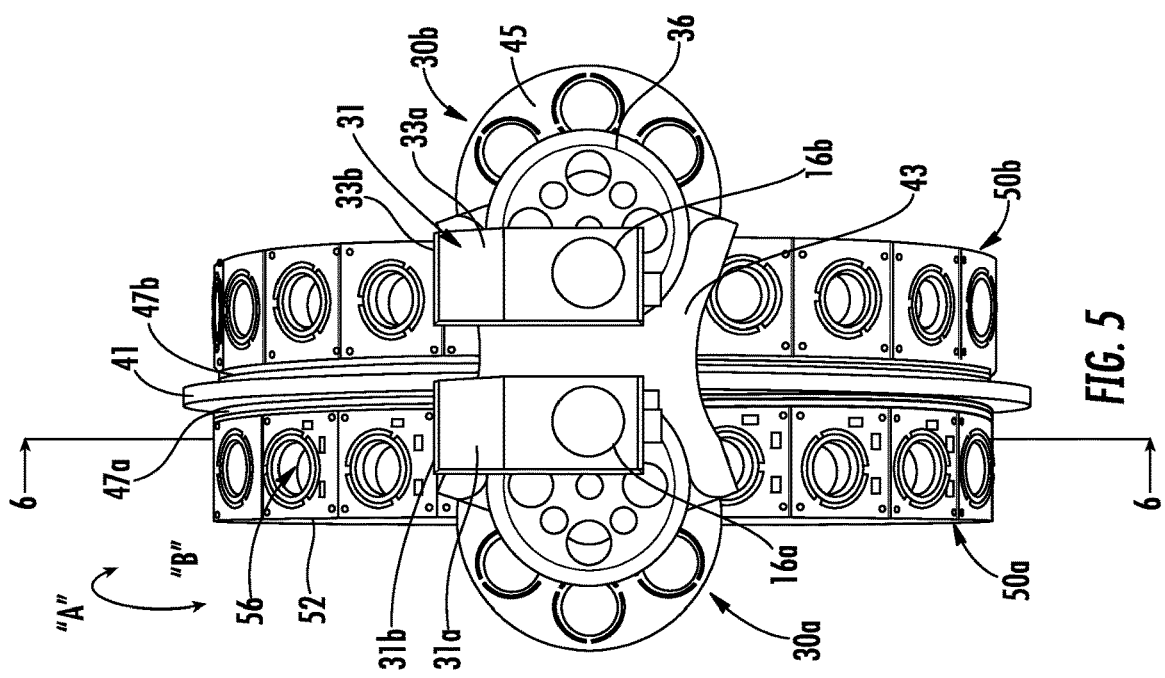
FIG. 5 is a front, perspective view of internal components of the refraction device of FIG. 1.
Figure 7:
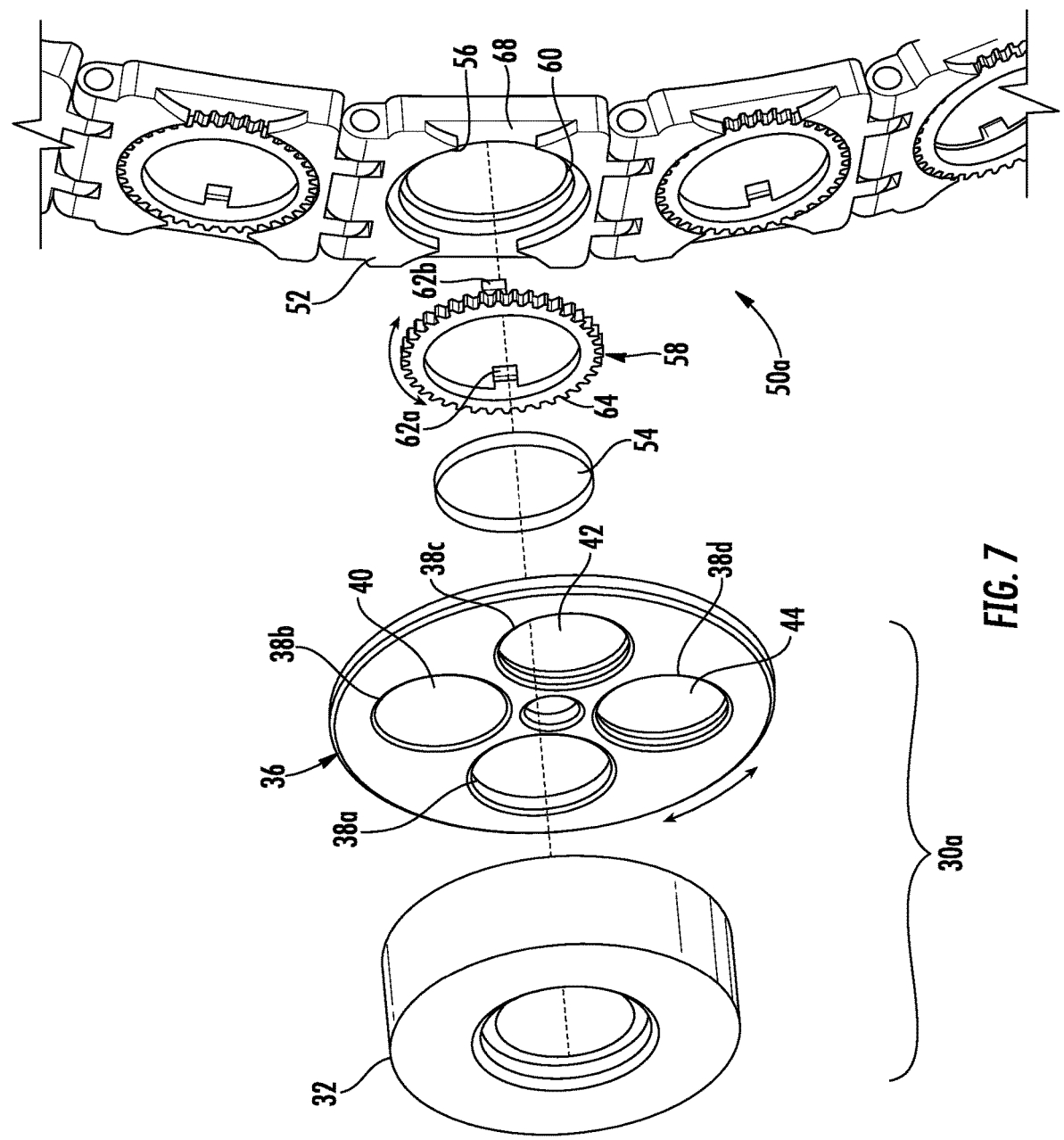
FIG. 7 is a perspective view, with parts separated, of an astigmatic power lens belt and a spherical power lens assembly of the refraction device of FIG. 1.

With reference to FIGS. 5-7, the belt 50a includes a plurality of brackets 52 fixed relative to one another. In embodiments, the brackets 52 may be pivotably coupled to one another via respective joints. Each of the plurality of brackets 52 defines an opening 56 therethrough having an astigmatic power lens assembly disposed therein. The astigmatic power lens assembly includes a friction ring 58, a motor 60, and an astigmatic power lens 54. The friction ring 58 has a pair of tabs 62a, 62b extending perpendicularly therefrom configured for snap-fitting engagement in the opening 56 of one of the brackets 52 while also permitting rotation of the friction ring 58 relative to and within the opening 56 of the bracket 52.

Each bracket 52 of the plurality of the brackets includes an astigmatic power lens 54 (e.g., a cylindrical power lens) having a discreet cylindrical power. The astigmatic power lenses 54 are fixed within the respective friction ring 58 such that a rotation of the friction ring 58 relative to the bracket 52 causes the astigmatic power lens 54 to rotate. The astigmatic power lenses 54 are each rotatable relative to their respective bracket 52 to adjust an axis of the astigmatic power lens 54 from 0° to 180° in steps of approximately 5°. It is contemplated that the astigmatic power lenses 54 may be configured to adjust an axis thereof in more or less than 5° steps.

Each bracket of the plurality of brackets 52 may include a motor 60 (e.g., a piezoelectric motor or a torque motor) operably coupled to the friction ring 58 for rotating the friction ring 58 and the associated astigmatic power lens 54 to adjust the axis thereof. The motor 60 may be disposed behind the friction ring 58 and have a hollow center to allow for the uninterrupted passage of light through the lens assembly and to the visual display 18. In some embodiments, the motor 60 may be disposed in a slot 68 defined in a side of the bracket 52.

The astigmatic power lenses 54 may vary in power in steps of 0.25D, 0.5D, 1.0D, 1.25D, 1.5D, 1.75D, 2.00D, or any other suitable step of diopter. The astigmatic power lenses 54 may also contain a spherical power, such as a "spherical equivalent," for example, a +0.50 diopter sphere combined with a −1.00 diopter cylinder. The astigmatic power lenses 54 are arranged on the belt 50a in sequential order based on power such that movement of the belt 50a relative to the main body 12 in a first rotational direction, indicated by arrow "A" in FIG. 5, will gradually increase the astigmatic power, and movement of the belt 50a relative to the main body 12 in a second rotational direction, indicated by arrow "B" in FIG. 5, will gradually decrease the astigmatic power. Since cylindrical axis adjustment is typically performed prior to cylindrical power adjustment, each of the astigmatic power lenses 54 may be configured to rotate simultaneously with one another so that each of the astigmatic power lenses 54 has the same axis.

The control 34 may be mechanically or electrically coupled to both the belt 50a as a whole and the discreet astigmatic power lenses 54 of the belt 50a for controlling movement of the belt 50a around the main body 12 and rotation of the astigmatic power lenses 54 relative to the respective brackets 52 of the belt 50a. The control 34 may be in communication with a power supply, a discreet controller, and/or other electronics such as a wireless transmitter and/or a receiver for transforming an actuation of the control 34 into movement of the belt 50a around the main body 12 and/or rotation of the astigmatic power lenses 54 relative to the respective brackets 52 of the belt 50a.

In some embodiments, instead of each bracket of the plurality of brackets 52 having a discreet motor 60 (e.g., a piezoelectric motor), the refraction device 10 may include one motor (not shown) disposed behind the first eyepiece 16a and operably coupled to an actuator (not shown), such as a gear or a screw. In this embodiment, outer teeth 64 of each of the friction rings 58 selectively operably couple to the actuator. As such, a rotation of the actuator via the motor effects a rotation of the selected friction gear 58 via the meshing engagement of the threading of the actuator and the teeth 64 of the friction gear 58. Due to the associated astigmatic power lens 54 being fixed to the friction ring 58, the associated astigmatic power lens 54 rotates in a corresponding direction to adjust its axis.

With reference to FIG. 1, the refraction device 10 further includes the visual display 18 disposed on the distal side 12b of the main body 12. The visual display 18 may be a flat-panel display, such as, for example, an LCD, an LED screen, or the like, formed with an inner wall of the distal side 12b of the main body 12. The visual display 18 may be configured as a heads-up-display ("HUD") integrally connected with the main body 12. The visual display 18 is spaced, along the optical pathways "P1," "P2," from the eyepieces 16a, 16b and the lens assemblies 30a, 30b. In this way, the visual display 18 is disposed on one side of the cavity 20 of the main body 12, and the eyepieces 16a, 16b and the lens assemblies 30a, 30b are disposed on an opposite of the cavity 20 of the main body 12. In embodiments, the refraction device 10 may include a holographic display (not shown) disposed behind the eyepieces 16a, 16b to display a hologram between the visual display 18 and a patient's eyes.

The visual display 18 is configured to display an eye chart used to test a visual acuity of a patient viewing the visual display 18 via the eyepieces 16a, 16b. The eye chart may be a LogMar chart, a Snellen chart, or any other suitable eye chart or vision target displayed on the visual display 18 in a format that is equivalent to reading an eye chart at a distance of approximately 20 feet or any suitable distance. In some embodiments, the visual display 18 may be configured to project a hologram of an eye chart in a format that is equivalent to reading the eye chart at a distance of approximately 20 feet or any suitable distance. The main body 12 may also include a speaker and/or headphones (not shown) in communication with the visual display 18 to synchronize a sound component with a video component of audiovisual media displayed on the visual display 18. Such an audiovisual system may be used to provide instructions to the patient regarding the operation of the refraction device 10.

The control 34 may be operable by a user to change the image displayed on the visual display 18. In embodiments, the visual display 18 may be in communication with a processor (not shown) operably connected to a memory, which may include transitory type memory (e.g., RAM) and/or non-transitory type memory (e.g., flash media, disk media, etc.). The processor may include software for running an eye examination. Those skilled in the art will appreciate that the processor may be substituted by using any logic processor (e.g., control circuit) adapted to perform the calculations and/or set of instructions described herein including, but not limited to, field programmable gate arrays, digital signal processor, and combinations thereof. The refraction device 10 may include a rechargeable internal power source for powering the visual display 18, or an electrical wire to be connected to an outside power source (e.g., a wall outlet) for powering the visual display 18.

In operation, a patient positions their eyes into the respective eyepieces 16a, 16b, or the eyepiece 17 (FIGS. 2A-C), with their forehead resting on the support member 28. The patient or a technician may activate an eye examination program saved in the memory of the refraction device 10 by moving or pressing the control 34. In embodiments, an eye examination program may begin automatically upon the sensors 26a-g sensing the patient's eyes. The visual display 18 may display a demonstration on how to operate the refraction device 10 and/or an image prompting the patient or technician to enter patient ID information (e.g., name, age, current lens prescription, insurance information, etc.), which may be stored in the memory and/or sent to a patient record system.

With the patient looking into the eyepieces 16a, 16b, the vertex distance and the pupillary distance of the patient's eyes may be determined in the manner described above. The prism assembly 31 may be activated to ensure that the light emitted from the visual display 18 passes through the diagnostic lenses into the patient's pupils. With the vertex distance of the patient's eyes set and the pupillary distance of the eyepieces 16a, 16b set, the visual display 18 may display an image of an eye chart, such as, for example, a LogMAR chart, and a sound recording or a visual cue may prompt the patient to perform a series of tasks. For example, spherical error of the patient's eyes may be tested by prompting the patient to read a line on the eye chart while the spherical power lens 32 has a 0.0D power, the blank opening 38a of the power wheel 36 is in line with the optical pathway "P1" of the first eyepiece 16a, and the blackout lens 38b is in line with the optical pathway "P2" of the right eyepiece 16b. The refraction device 10 may also measure the patient's pupil size at various distances and lighting conditions.

Based on which line the patient is able to read, the visual display 18 may display another image such as a word, a line, or a series of lines. The patient may then be prompted again to view the new image and to actively adjust the spherical power of the spherical power lens 32 in 0.25D increments until they see the image clearly. This process may continue for any suitable number of iterations until the spherical error in the patient's left eye is precisely determined. Once the patient is able to see the image(s) clearly, the spherical power of the spherical power lens 32 selected by the patient is stored in the memory of the refraction device 10 as the spherical error in the patient's left eye. This process may be repeated to determine the spherical power error in the patient's right eye.

In addition to testing for the spherical power error in the patient's eyes, the patient may also be tested for astigmatism. Astigmatism is tested using the belts 50a, 50b of the refraction device 10 and the cylindrical fine adjustment wheel 45 (FIG. 5). To test for astigmatism, the axis of the patient's eye is determined and then the cylindrical power of the patient's eye is determined. To determine the axis, any astigmatic power lens 54 of the plurality of astigmatic power lenses 54 is disposed in line with the optical pathway "P1" of the first eyepiece 16a.

While viewing an image (e.g., a word, a line, or an object) on the visual display 18, the patient adjusts the axis of the astigmatic power lens 54 by rotating the astigmatic power lens 54 relative to the bracket 52. In particular, the patient may move or rotate the control 34 to activate the piezoelectric motor 60 associated with the bracket 52, thereby rotating the astigmatic power lens 54 relative to the bracket 52. The patient continues to rotate the astigmatic power lens 54 until they see the image displayed on the visual display 18 substantially clearly. Once the patient is able to see the selected image substantially clearly, the axis selected by the patient for that eye is stored in the memory of the refraction device 10 as the axis error in the patient's left eye. As briefly mentioned above, each of the astigmatic power lenses 54 may be configured to rotate in synchrony with one another such that all of the astigmatic power lenses 54 have the selected axis.

With the axis set, the patient rotates or moves the control 34 to effect a rotation of the belt 50a around the circular channel of the main body 12 to adjust the cylindrical power of the refraction device 10. Rotation of the belt 50a relative to the main body 12 moves one astigmatic power lens 54 out of alignment with the optical pathway "P1" of the first eyepiece 16a and positions an adjacent astigmatic power lens 54, having a different cylindrical power, in alignment with the optical pathway "P1." The patient continuously views the image displayed on the visual display 18 as they increase or decrease the cylindrical power of the refraction device 10 using the control 34. If the image continues to appear blurry, the patient will activate another discreet movement of the belt 50a to position another astigmatic power lens 54, having another cylindrical power, in line with the optical pathway "P1" of the first eyepiece 16a.

The patient continues to adjust the cylindrical power of the refraction device 10 via rotation of the belt 50a until the image appears substantially clear. Once the patient is able to see the selected image clearly, the cylindrical power of the astigmatic power lens 54 selected by the patient is stored in the memory of the refraction device 10 as the cylindrical power error in the patient's left eye. This process may be repeated to determine the cylindrical axis error and the cylindrical power error in the patient's right eye.

At this point, the spherical power error, the cylindrical axis error, and the cylindrical power error for both eyes, and the visual acuity obtained with the best combination of lenses, is determined and saved in the memory of the refraction device 10 and/or sent to a patient record system. The determined spherical power error, cylindrical axis error, and cylindrical power error for both eyes may then be used to generate a prescription for corrective lenses.

It is contemplated that the refraction device 10 may include a plurality of distinct controls such as dials, knobs, switches, or the like, linked to the various components of the refraction device 10 for activating said components (e.g., the belts 50a, 50b, the spherical power lenses 30, and the astigmatic power lenses 54).

With reference to FIGS. 8-13B, the refraction device 10 may further include a prism lens assembly 70 to test and correct for ocular misalignment due to strabismus (e.g., a phoria and/or a tropia). The prism lens assembly 70 is configured to change the direction of light passing through it to displace an image displayed on the visual display 18 in a particular direction depending on the type and degree of ocular misalignment. The prism lens assembly 70 may be moved in a plurality of directions around the optical pathways "P1," "P2." In addition, the prism lens assembly 70 may be an adjustable or tunable prism lens to allow for the power of the prism to be changed in one prism diopter increments. In some embodiments, a rotational (e.g., cyclo-torsional) phoria may be tested using an infrared sensor directed at a surface of a patient's eyes.

Figure 8:
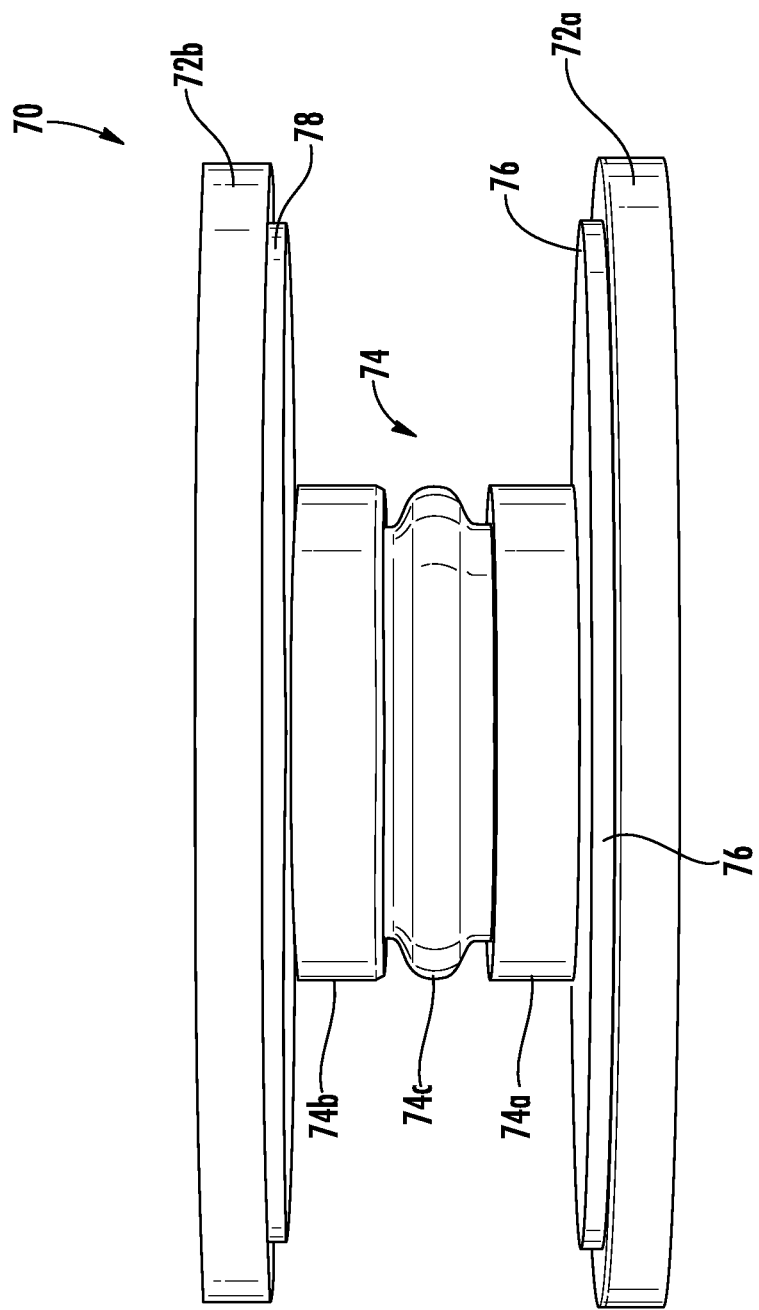
FIG. 8 is a top view of a tunable prism lens assembly for use in the refraction device of FIG. 1.
Figure 9:
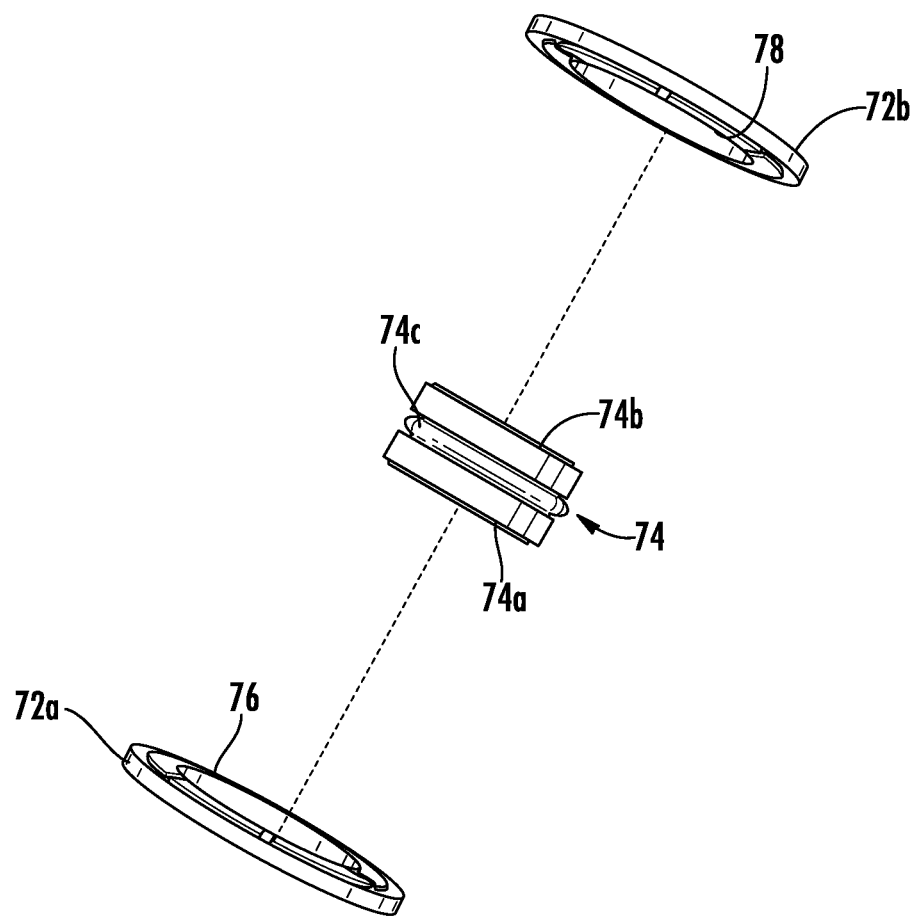
FIG. 9 is a perspective view, with parts separated, of the tunable prism lens assembly of FIG. 8.
Figure 10:
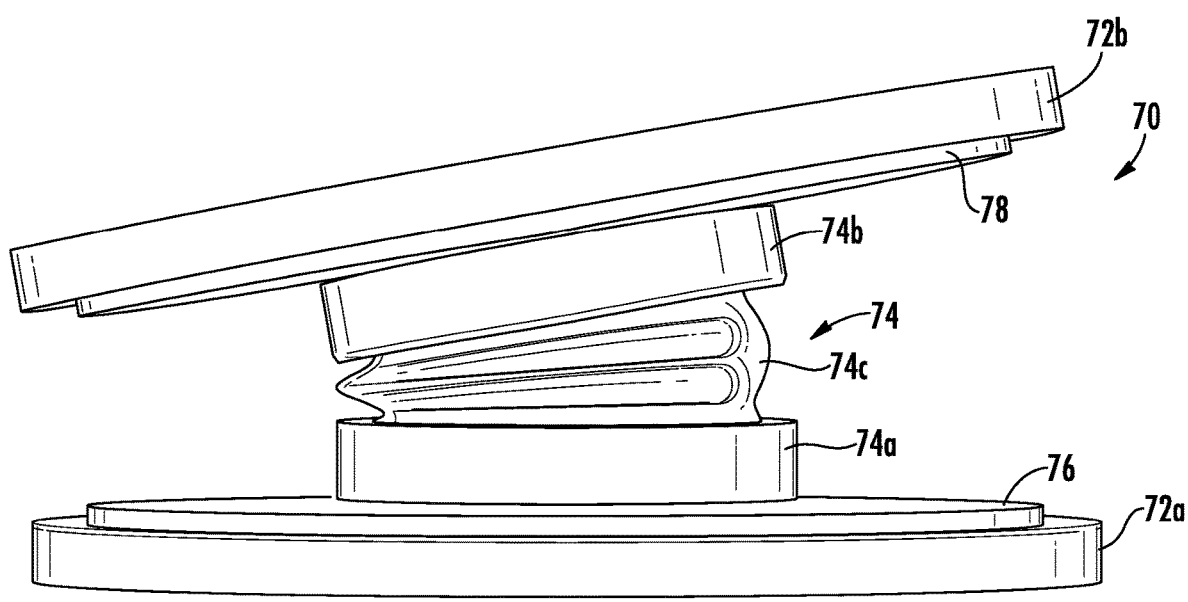
FIG. 10 is a top view of the tunable prism lens assembly of FIG. 8 illustrated in a non-linear configuration.

For example, with reference to FIGS. 8-10, one embodiment of a prism lens assembly 70 to test and correct for ocular misalignment due to strabismus is illustrated. A first prism lens assembly 70 may be disposed in front of or behind the first lens assembly 30a (FIG. 5) and in line with the first optical pathway "P1," and a second tunable prism lens assembly 70 may be disposed in front of or behind the second lens assembly 30b and in line with the second optical pathway "P2." The tunable prism lens assemblies 70 may include a pair of outer plates 72a, 72b and an inner optical element 74, similar to the optical element 39 described above, (e.g., a tunable prism, such as the tunable prism sold by Optotune®).

The optical element 74 is disposed between the outer plates 72a, 72b, and includes two outer lenses 74a, 74b and an inner membrane or diaphragm 74c pivotably coupling the outer lenses 74a, 74b to one another. Upon pivoting the outer lenses 74a, 74b relative to one another about the inner diaphragm 74c, the optical element 74 is transitioned from a linear configuration to a non-linear configuration. In the linear configuration, light passes linearly through the optical element 74. In the non-linear configuration, light passes from the first outer lens 74a of the optical element 74 in a first direction, and is then shifted as it passes through the diaphragm 74c and the second outer lens 74b. In this way, manipulation of the optical element 74 provides control over the direction light that passes through it.

The first outer plate 72a of the prism lens assembly 70 is fixed to the first outer lens 74a of the optical element 74 and is also fixed within the main body 12 (FIG. 1) of the refraction device 10. The second outer plate 72b is fixed to the second outer lens 74b of the optical element 74 while being free to pivot within the main body 12 of the refraction device 10 and relative to the first outer lens 74a. The first and second outer plates 72a, 72b define holes (not shown) therethrough to allow for light to pass therebetween. The first outer plate 72a may include a plurality of circumferentially-disposed electromagnetic coils 76 fixed thereto, and the second outer plate 72b may include a plurality of circumferentially-disposed permanent magnets 78 fixed thereto. The electromagnetic coil(s) 76 receive current from a power source to generate a magnetic field, thereby attracting the permanent magnet(s) 78 on the second outer plate 72b to move the second outer plate 72b, and in turn the second outer lens 74b of the optical element 74, relative to the first outer plate 72a. As such, the direction and degree of pivoting of the second outer lens 74b of the optical element 74 may be controlled by controlling the amount of current and in which electromagnetic coil 76 the current is delivered.

In use, if a patient does not have strabismus in either eye, the prism lens assemblies 70 are maintained in their linear configuration allowing light to pass linearly therethrough. However, if a patient does have strabismus, the patient's pupil or pupils will not be aligned with the optical pathway, as will be detected by the sensors 26a-g (FIG. 3B). To bring the optical pathway into alignment with the patient's pupil(s), the optical element 74 of the prism lens assembly 70 is adjusted (either manually or automatically using information gathered by the sensors 26a-g) using the electromagnetic coils 76 and the permanent magnet 78 of the outer plates 72a, 72b, as described above.

As the optical element 74 of the prism lens assembly 70 is adjusted, the light passes through the optical element 74 in a first direction, and is redirected out of the optical element 74 at a different angle toward the patient's pupil(s). Whether the prism lens assembly 70 is adjusted manually or automatically, the angle of the optical element 74 in which the optical pathway is aligned with the patient's pupil(s) may be saved to a memory of the refraction device 10. The determined angle may be directly correlated with the degree of correction required for the patient's ocular misalignment. With this information, a prescription for a prism lens may be determined.

Figure 11:
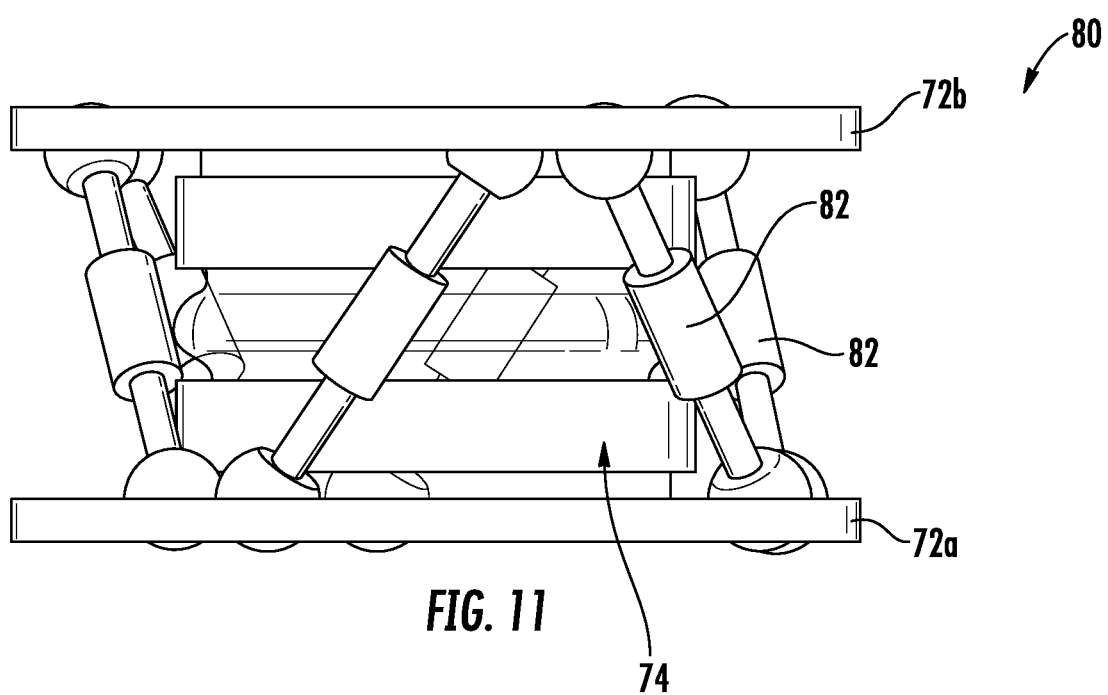
FIG. 11 is a top view of another embodiment of a tunable prism lens assembly for use in the refraction device of FIG. 1.

With reference to FIG. 11, another embodiment of a tunable prism lens assembly 80 is illustrated, similar to the prism lens assembly 70 described above. The tunable prism lens assembly 80 includes the optical element 74 disposed between the outer plates 72a, 72b. Instead of using electromagnetism to change the configuration of the optical element 74, the tunable prism lens assembly 80 includes a plurality of pistons 82 extending between the plates 72a, 72b at a transverse angle. The length of the pistons 82 are adjusted to change the configuration of the optical element 74. It is contemplated that the pistons 82 may be powered using hydraulics, pneumatics, electronics, magnetic, or the like.

Figure 12A:
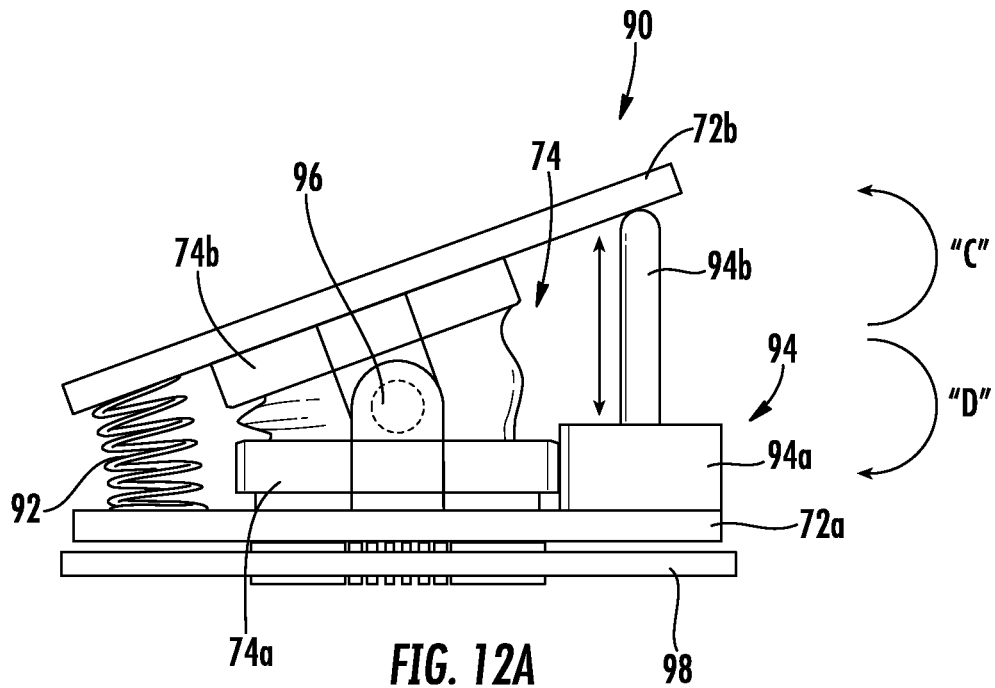
FIG. 12A is a top view of yet another embodiment of a tunable prism lens assembly for use in the refraction device of FIG. 1.
Figure 12B:
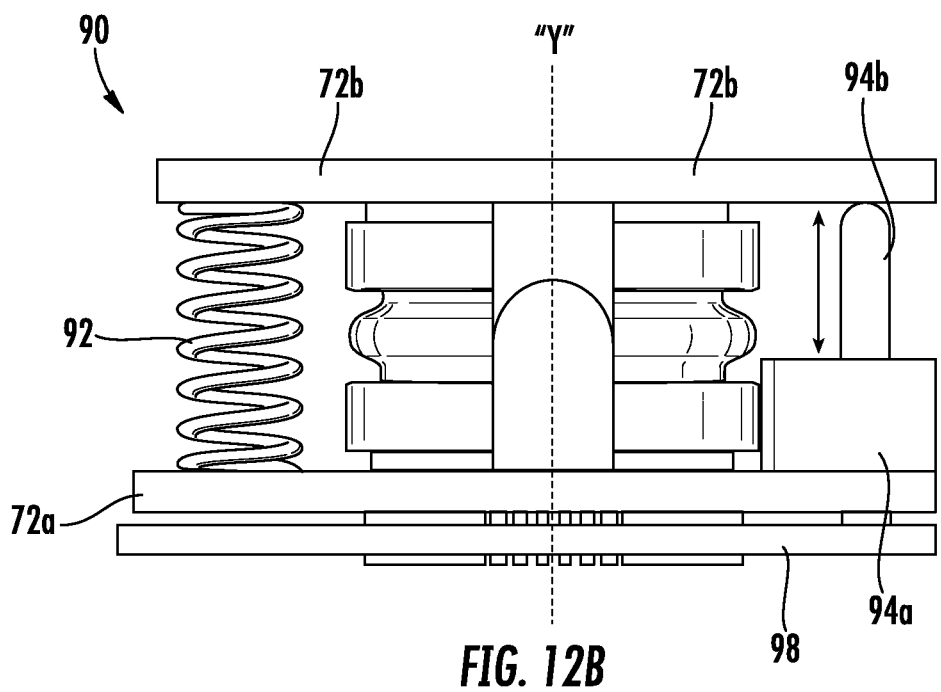
FIG. 12B is a top view of the tunable prism lens assembly of FIG. 12A illustrated in a linear configuration.

With reference to FIGS. 12A and 12B, another embodiment of a tunable prism lens assembly 90 is illustrated, similar to the tunable prism lens assembly 70 described above. The prism lens assembly 90 includes the optical element 74 disposed between the outer plates 72a, 72b. Instead of using electromagnetism to change the configuration of the optical element 74, the prism lens assembly 90 includes a biasing member 92 (e.g., a coil spring) and a linear actuator 94. The biasing member 92 and the linear actuator 94 are disposed on opposite sides of the optical element 74 and each extends between the plates 72a, 72b. The first and second plates 72a, 72b are pivotably coupled to one another via a pivot assembly 96 that allows the second plate 72b to pivot relative to the first plate 72a about a pivot axis. The linear actuator 94 includes a motor 94a and a rod or pin 94b operably coupled to the motor 94. Upon actuating the motor 94a, the motor 94a drives linear movement of the pin 94b either toward the second plate 72b or away from the second plate 72b.

To pivot the second plate 72b in a first direction, indicated by arrow "C" in FIG. 12A, the pin 94b is raised into engagement with an underside of a first side of the second plate 72b to pivot the second plate 72b against the resilient bias of the biasing member 92. To pivot the second plate 72b in a second direction, indicated by arrow "D" in FIG. 12A, the pin 94b is lowered allowing the biasing member 92 to pivot the second plate 72b in the second direction. A support plate 98 may be provided on which the first plate 72a is rotatably supported. The support plate 98 is configured to rotate the prism lens assembly 90 about an axis "Y" extending through the length of the optical element 74. In this way, the support plate 98 and the linear actuator 94 together provide multiple degrees of freedom in changing the orientation of the second lens 74b of the optical element 74. In embodiments, rather than having the prism lens assembly 90 rotatable supported on the support plate 98, the prism lens assembly 90 may be rotationally fixed relative to the support plate 98 while the support plate 98 is rotatably supported in the main body 12 (FIG. 1) of the refraction device 10.

In embodiments, the refraction device 10 may include a color vision test, a device for testing intraocular pressure, an iris identification sensor, a pupil measurement capacity, OCT technology, and/or a device for testing corneal thickness. In embodiments, the eyepieces 16a, 16b may be modular eyepieces that are removable from the main body 12 and replaced with a diagnostic tool, such as, for example, any tools used to determine the above-mentioned vision deficiencies or vision characteristics. In embodiments, the refraction device 10 may be configured to measure the diameter of a patient's pupil. The diameter of the patient's pupil may be measured in variable amounts of light incident upon the eye using a light source provided in the refraction device 10 or a secondary light source.

Figure 13A:
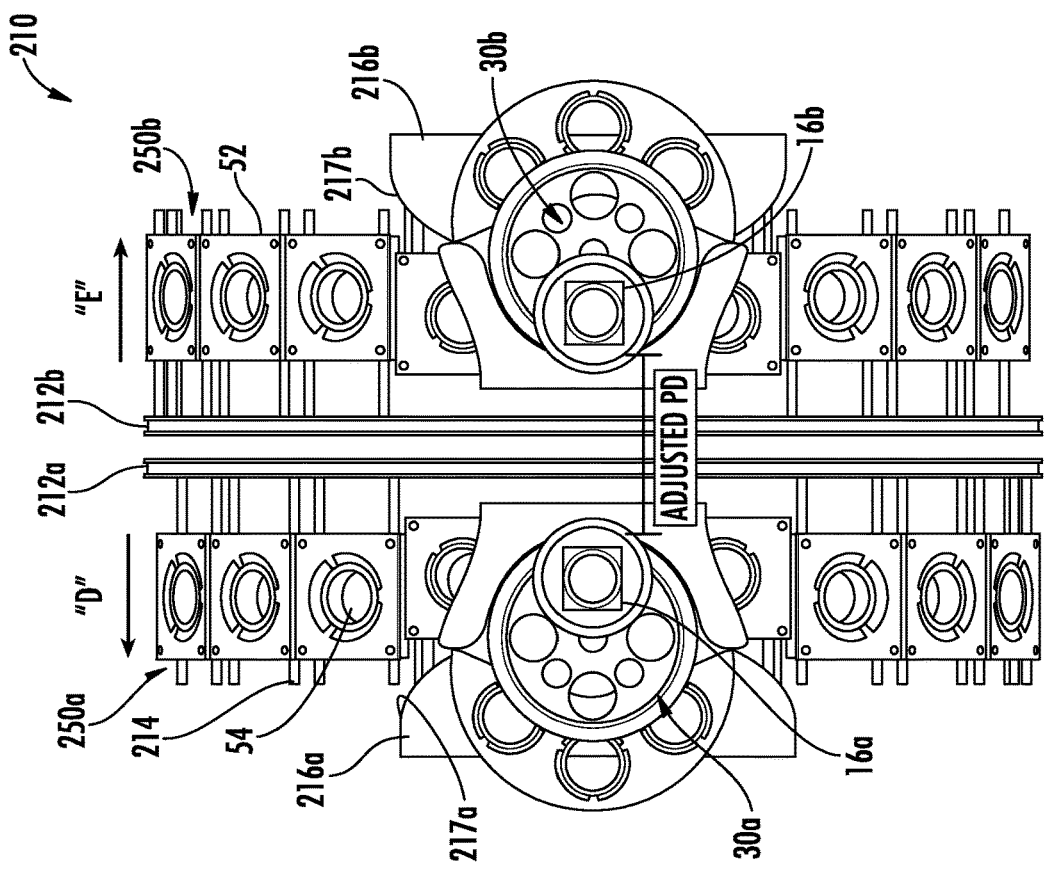
FIG. 13A is a front view, with parts removed, of another embodiment of a refraction device for determining refractive errors of a patient's eye(s)
Figure 13A:
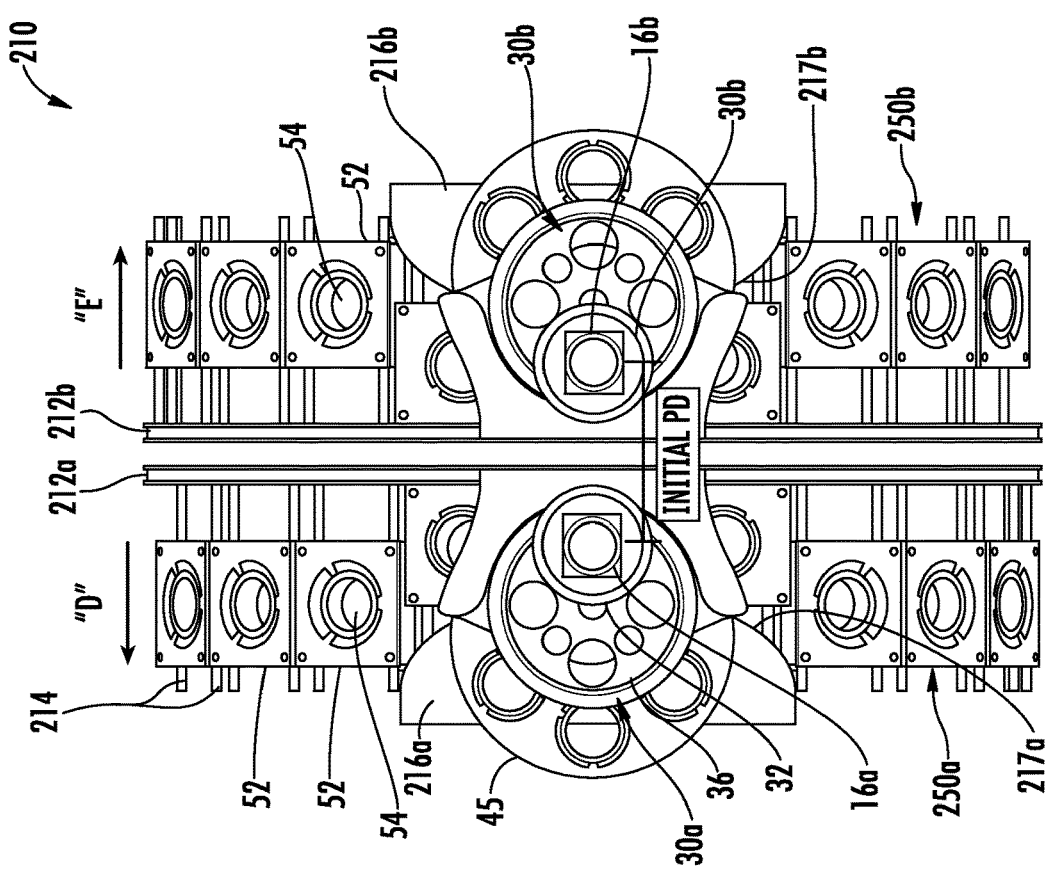
Figure 14:
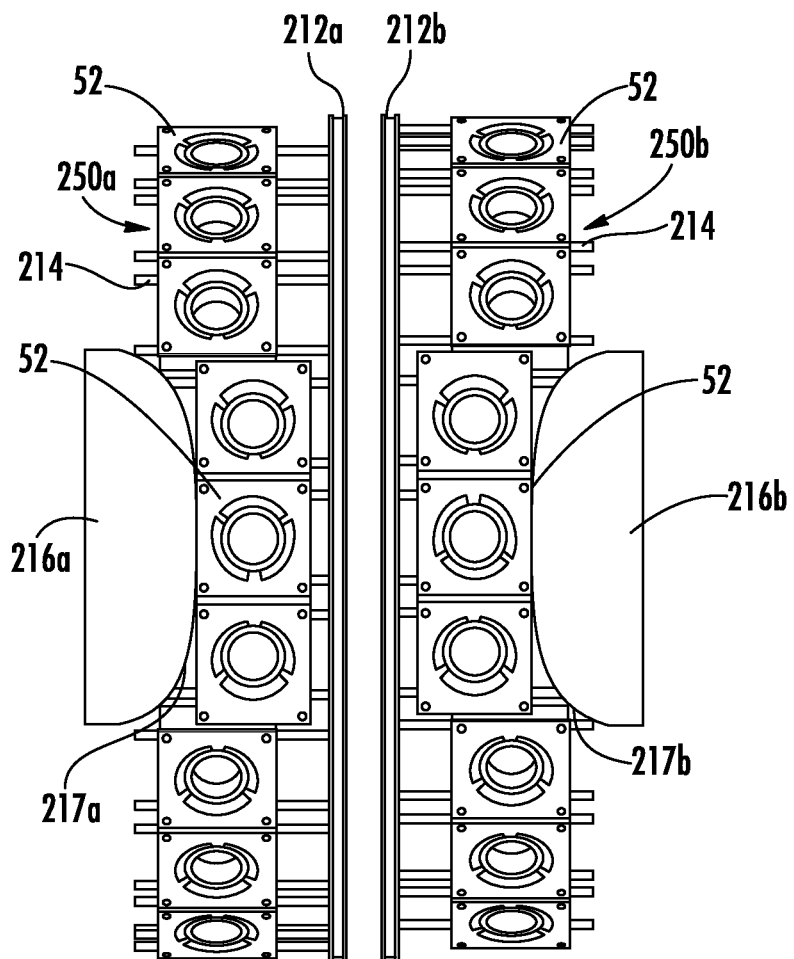
FIG. 14 is a front view, with parts removed, of the refraction device of FIG. 13A illustrating lens guide blocks.

With reference to FIGS. 13A, 13B, and 14, inner components of another embodiment of a refraction device 210 is illustrated. Due to the substantial similarities between the refraction device 210 of the present embodiment and the refraction device 10 described above, only certain selected features of the refraction device 210 will be described in detail herein. The refraction device 210 includes a main body (not shown), similar to the main body 12 of refraction device 10, a visual display (not shown), similar to the visual display 18 of refraction device 10, and the diagnostic lenses (e.g., the astigmatic power lenses 54 and the lens assemblies 30a, 30b) described above. However, instead of each of the diagnostic lenses of the refraction device 210 being fixed in a horizontal position, the refraction device 210 of the present embodiment allows for horizontal movement of the diagnostic lenses to match the PD of the patient's eyes. This is in contrast to the refraction device 10 described above, which uses the prism assembly 31 (FIG. 6) to ensure the optical pathway extends through the diagnostic lenses and into the patient's pupils.

The eyepieces 16a, 16b and the lens assemblies 30a, 30b of the refraction device 210 are slidably coupled to the main body. As such, the first eyepiece 16a and the first lens assembly 30a may be moved (e.g., either manually or automatically) horizontally relative to the main body as one unit (hereinafter "first lens unit"), and the second eyepiece 16b and the second lens assembly 30b may be moved horizontally relative to the main body as one unit (hereinafter "second lens unit").

In particular, the refraction device 210 includes a pair of rotatable wheels 212a, 212b having a plurality of circumferentially-disposed supports or rails 214 extending laterally therefrom. The rails 214 slidably support each of the brackets 52 and their associated astigmatic power lens 54. The first wheel 212a supports the brackets 52 of a first belt 250a, and the second wheel 212b supports the brackets 52 of the second belt 250b. As such, the belts 250a, 250b are movable along a circular pathway with rotation of the respective wheels 212a, 212b, while the individual brackets 52 of each of the belts 250a, 250b are horizontally movable relative to the wheels 212a, 212b along the rails 214 to match the selected bracket 52 with the PD of the patient. Each of the brackets 52 are resiliently biased in an outer direction, indicated by arrows "D," "E" in FIG. 13A. For example, a biasing member (not shown) may be disposed between the wheel 212a and the bracket 52.

With continued reference to FIGS. 13A, 13B, and 14, the refraction device 210 includes first and second guide blocks 216a, 216b slidably supported in the main body. The first guide block 216a is fixedly coupled to the first lens unit, and the second guide block 216b is fixedly coupled to the second lens unit, such that the first and second guide blocks 216a, 216b move horizontally with the first and second lens units. The first guide block 216a has a curved inner surface 217a in contact with an outer surface of at least one bracket 52 of the first belt 250a, and the second guide block 216b has a curved inner surface 217b in contact with an outer surface of at least one bracket 52 of the second belt 250b.

In use, the first and second lens units may be adjusted, either manually by a patient or automatically based on information regarding the PD of the patient sensed by sensors, such as the sensors 26a-g of FIG. 3B, to match the PD of the patient. As the first and second lens units are moved horizontally from an initial position, as shown in FIG. 13A, to an adjusted position, as shown in FIG. 13B, the guide blocks 216a, 216 also move to push at least one bracket 52 of each of the first and second belts 250a, 250b horizontally along the rails 214 to align the associated astigmatic power lenses 54 with the patient's eyes. To position a different astigmatic power lens 54 in line with the patient's eyes, the one or both of the first and second wheels 212a, 212b are rotated. As the first and second wheels 212a, 212b are rotated, and in turn the first and second belts 250a, 250b, the brackets 52 move along the curved inner surfaces 216a, 217b of the first and second guides 216a, 216b, whereby the brackets 52 are pushed inwardly in the horizontal direction, against the outwardly-oriented resilient bias, to align the selected bracket 52 with the patient's eyes.

With reference to FIGS. 15A and 15B, an eye examination system 100 is illustrated and includes another embodiment of a refraction device 110, which may be supported on a table 115. The refraction device 110 is substantially similar to the refraction devices 10, 210 described above. Accordingly, the refraction device 110 of the present embodiment will only be described in the detail necessary to elucidate selected differences from the refraction devices 10 and 210.

The refraction device 110 includes a main body 112 supported on a base 114. The main body 112 has a pair of eyepieces 116a, 116b extending proximally from a proximal side thereof. Instead of having a face mount to adjust the distance between a patient's eyes and a lens assembly of the refraction device 110, the eyepieces 116a, 116b have an adjustable length. The main body 112 includes a pair of handles 117a, 117b disposed adjacent the respective eyepieces 116a, 116b for moving the main body 112 relative to the base 114 in a plurality of directions.

The main body 112 is coupled to the base 114 and rotatable relative to the base 114 in three degrees of freedom. In particular, the base 114 includes a platform 120 supported on a stable surface such as a top of the table 115, and an arm 122 extending upwardly from the platform 120. The arm 122 has a first end 122a and a second end 122b and has an arcuate configuration. The first end 122a of the arm 122 is coupled to the platform 120 via a slider 124 such that the arm 122 is slidable along and relative to a horizontal axis "H" defined by the platform 120. The slider 124 is also rotatably coupled to the platform 120 to allow for the first end 122a of the arm 122 to rotate about an axis extending perpendicularly from the table 115.

The first end 122a of the arm 122 and the slider 124 support a bottom portion 112a of the main body 112. The first end 122a of the arm 122 may extend through an arcuate channel (not shown) defined through the slider 124. The first end 122a of the arm 122 may also be configured to move relative to the slider 124 to adjust an amount the first end 122a of the arm 122 projects from the slider 124.

The second end 122b of the arm 122 of the base 114 pivotably supports a top portion 112b of the main body 112. To change a yaw angle of the refraction device 110, the main body 112 may be rotated relative to the arm 122 about the pivotal connection between the top portion 112b of the main body 112 and the second end 122b of the arm 122. Since the top portion 112b of the main body 112 is coupled to the second end 122b of the arm 122, as the first end 122a of the arm 122 is moved through and relative to the slider 124, the second end 122b of the arm 122 rotates the main body 112 to change a roll angle of the refraction device 110 and/or a pitch angle of the refraction device 110. The table 115 may include height-adjustable legs 119 to move the refraction device 110 along a vertical axis "Y" to a selected height.

In some embodiments, the base 14 of the refraction device 10 may be replaced with the base 114 of the refraction device 110.

Figure 16A:
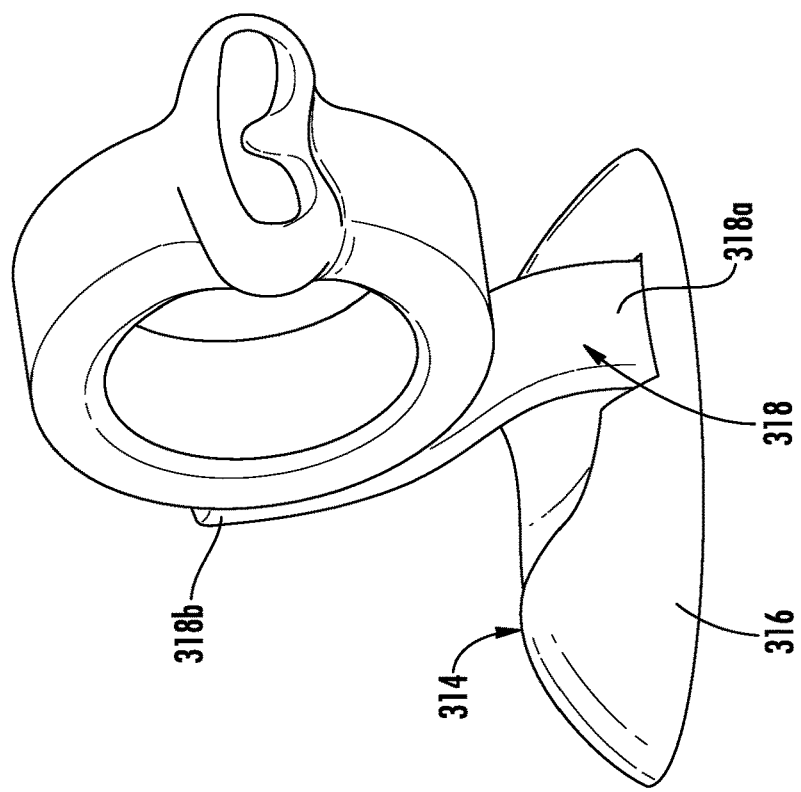
FIG. 16A is a perspective view of another embodiment of a base having a refraction device of the present disclosure supported thereon.
Figure 16B:
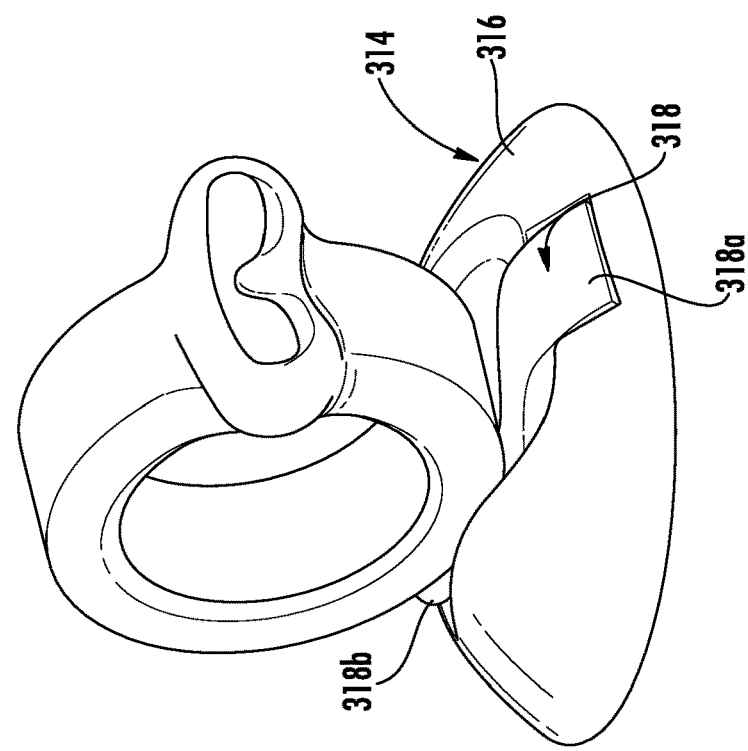
FIG. 16B is a perspective view of the base of FIG. 16 illustrated in an extended position.

With reference to FIGS. 16A and 16B, another embodiment of a base 314 is illustrated. The base 314 includes a stand 316 and an arm 318. The arm 318 has a first end 318a pivotably coupled to the stand 316, and a second end 318b on which the main body of the refraction device is rotatably supported. In another embodiment, the arm 318 may comprise a plurality (e.g., two) segments linked to one another via a joint, such as, for example, a hinge.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A refraction device, comprising:
  a main body;
  a first diagnostic lens assembly for testing visual acuity of a first eye of a patient, the first diagnostic lens assembly coupled to the main body and including:
    a first spherical power lens; and
    a first plurality of astigmatic power lenses;
  a second diagnostic lens assembly for testing visual acuity of a second eye of the patient, the second diagnostic lens assembly coupled to the main body and including:
    a second spherical power lens spaced laterally from the first spherical power lens; and
    a second plurality of astigmatic power lenses; and
  a visual display integrally connected to the main body and oriented toward first and second optical pathways extending through the respective first and diagnostic lens assemblies, the visual display configured to display an image for testing visual acuity.

2. The refraction device according to claim 1, wherein each astigmatic power lens of the first plurality of astigmatic power lenses being configured to be selectively moved between a position in line with the first spherical power lens, and a position out of line with the first spherical power lens.

3. The refraction device according to claim 2, further comprising a belt disposed within the main body, the belt having the first plurality of astigmatic power lenses associated therewith.

4. The refraction device according to claim 3, wherein at least one astigmatic power lens of the first plurality of astigmatic power lenses is rotatable relative to the belt.

5. The refraction device according to claim 3, wherein the belt is movable relative to the main body to position a selected astigmatic power lens of the first plurality of astigmatic power lenses in line with the first spherical power lens.

6. The refraction device according to claim 5, wherein the belt has an arcuate configuration such that the belt is movable relative to the main body along a circular pathway.

7. The refraction device according to claim 3, wherein the belt has a plurality of brackets coupled to one another, each astigmatic power lens of the first plurality of astigmatic power lenses being coupled to a respective bracket of the plurality of brackets.

8. The refraction device according to claim 7, wherein a first astigmatic power lens of the first plurality of astigmatic power lenses is rotatable relative to the respective bracket of the plurality of brackets to adjust an axis of the first astigmatic power lens.

9. The refraction device according to claim 2, further comprising a plurality of brackets disposed within the main body, wherein each astigmatic power lens of the first plurality of astigmatic power lenses being coupled to a respective bracket of the plurality of brackets.

10. The refraction device according to claim 9, wherein a first astigmatic power lens of the first plurality of astigmatic power lenses is rotatable relative to the respective bracket of the plurality of brackets to adjust an axis of the first astigmatic power lens.

11. The refraction device according to claim 9, wherein the plurality of brackets are coupled to one another and are disposed in an annular array.

12. The refraction device according to claim 9, further comprising a wheel rotatably supported in the main body, wherein the plurality of brackets are circumferentially disposed on the wheel.

13. The refraction device according to claim 12, wherein the rotatable wheel includes a plurality of circumferentially-disposed rails extending laterally therefrom, the plurality of brackets being slidably supported on the plurality of rails such that a horizontal position of the plurality of brackets relative to the wheel is adjustable to align a selected one of the first plurality of astigmatic power lenses with a patient's pupil.

14. The refraction device according to claim 1, further comprising a tunable prism disposed in line with the first spherical power lens and at least one astigmatic power lens of the first plurality of astigmatic power lenses, wherein the tunable prism is configured to redirect light passing from the visual display to a patient's eye.

15. The refraction device according to claim 1, further comprising a prism lens assembly disposed in line with the first spherical power lens and a first astigmatic power lens of the first plurality of astigmatic power lenses, wherein the prism lens assembly is movable between a linear configuration, in which light passes linearly therethrough, and at least one non-linear configuration, in which the prism lens assembly redirects light passing therethrough.

16. The refraction device according to claim 15, wherein the prism lens assembly includes:
a pair of outer plates; and
an inner optical element disposed between the outer plates, wherein at least one plate of the pair of outer plates is movable to adjust the inner optical element between the linear and at least one non-linear configurations.

17. The refraction device according to claim 1, wherein the visual display is a heads-up display disposed on a distal side of the main body, the heads-up display configured to display an eye chart.

18. The refraction device according to claim 1, wherein the visual display is configured to project a hologram of an eye chart in a format that is equivalent to reading the eye chart at a distance of approximately 20 feet.

19. The refraction device according to claim 1, wherein the main body defines a cavity therein, the visual display being spaced across the cavity from each of the first and second diagnostic lens assemblies.

20. A patient-operable refraction device, comprising:
a main body;
a first diagnostic lens assembly for testing visual acuity of a first eye of a patient, the first diagnostic lens assembly coupled to the main body and including:
a first spherical power lens; and
a first plurality of astigmatic power lenses;
a second diagnostic lens assembly for testing visual acuity of a second eye of the patient, the second diagnostic lens assembly coupled to the main body and including:
a second spherical power lens spaced laterally from the first spherical power lens; and
a second plurality of astigmatic power lenses;
a plurality of brackets disposed within the main body, the plurality of brackets having the first and second plurality of astigmatic power lenses associated therewith, wherein the plurality of brackets are movable relative to the main body to position a selected astigmatic power lens of the plurality of first and second astigmatic power lenses in line with the respective first and second spherical power lenses; and
a visual display coupled to the main body and oriented toward an optical pathway extending through the first and second diagnostic lens assemblies, the visual display configured to display an image for testing visual acuity.

* * * * *